United States Patent [19]

Chivers et al.

[11] Patent Number: 5,578,564
[45] Date of Patent: Nov. 26, 1996

[54] NICKEL-FREE HEMOGLOBIN AND METHODS FOR PRODUCING SUCH HEMOGLOBIN

[75] Inventors: Mark L. Chivers, Arvada; Thomas K. Belval, Broomfield, both of Colo.

[73] Assignee: Somatogen, Inc., Boulder, Colo.

[21] Appl. No.: 97,273

[22] Filed: Jul. 23, 1993

[51] Int. Cl.$^6$ .................................................. A61K 37/02
[52] U.S. Cl. ............................... 514/6; 530/385; 540/145
[58] Field of Search ............................. 540/145; 514/6; 530/385

[56] References Cited

U.S. PATENT DOCUMENTS

| | | | |
|---|---|---|---|
| 4,301,144 | 11/1981 | Iwashita et al. | 424/78 |
| 4,321,259 | 3/1982 | Nicolau et al. | 424/101 |
| 4,336,248 | 6/1982 | Bonhard | 424/101 |
| 4,377,512 | 3/1983 | Ajisaka et al. | 424/78 |
| 4,412,989 | 11/1983 | Iwashita et al. | 424/177 |
| 4,473,563 | 9/1984 | Nicolau et al. | 424/224 |
| 4,598,064 | 7/1986 | Walder | 514/6 |
| 4,600,531 | 7/1986 | Walder | 530/385 |
| 4,650,786 | 3/1987 | Wong | 514/6 |
| 4,670,417 | 6/1987 | Iwasaki et al. | 424/78 |
| 4,710,488 | 12/1987 | Wong | 514/6 |
| 4,831,012 | 5/1989 | Estep | 514/6 |
| 4,857,636 | 8/1989 | Hsia | 530/385 |
| 4,861,867 | 8/1989 | Estep | 530/385 |
| 4,952,684 | 8/1990 | Yalpani et al. | 536/32 |
| 5,057,302 | 10/1991 | Johnson et al. | 514/6 |
| 5,084,558 | 1/1992 | Rausch | 530/385 |
| 5,194,590 | 3/1993 | Sehgal et al. | 530/385 |
| 5,438,041 | 8/1995 | Zheng et al. | 514/6 |

FOREIGN PATENT DOCUMENTS

| | | |
|---|---|---|
| 0073888 | 3/1983 | European Pat. Off. . |
| 8700177 | 1/1987 | WIPO . |
| 91/00290 | 6/1990 | WIPO . |
| 9211283 | 7/1992 | WIPO . |

OTHER PUBLICATIONS

Leach, C. N., et al/Serum Nickel Concentrations in Patients wit Unstable Angina and Myocardial Infarction/Ann. Clin. Lab. Sci./(1984), 14(5), 414–415.

Sarkar, B./Nickel Metablolism/Nickel in the Human Environment/Pub: Int. Agency for Res. on Cancer, Lyon, France/(1984), 367–384.

Leach, C. A. & Sunderman, W./Hypernickelemia Induced by Nickel Contamination of Radiographic Contrast Media/Ann. Clin. Lab. Sci./(1986), 16(4), 327–328.

Haner, M. et al/synthesis of Affinity–Label Chelates: A Novel Synthetic Method of Coupling Ethylenediaminetetraacetic Acid to Amine Functional Groups/Arch. of Biochem. & Biophys./(1984), 231(2), 477–486.

Haner, M. et al/Synthesis of a New Chelating Gel: Removal of $Ca^{2+}$ Ions from Parval–Bumin/Anal. Biochemistry/(1984), 138, 229–234.

Kilburn, K. H. et al/Cross–Shift and Chronic Effects of Stainless–Steel Welding Related to Internal Dosimetry of Chromium and Nickel/Am. J. of Indust. Med./(1990), 17, 607–615.

Knight, J. A. et al/Pulmonary Bronchoalveolar Hyperplasia in Rats after Protracted Parenteral Injections of Nickel Chloride/Ann. Clin. & Lab. Sci./(1987), 17(4), 275.

Knight, J. A. et al/Pathological Reactions in Lung, Liver, Thymus, and Spleen of Rats after Subacute Parenteral Administration of Nickel Sulfate/Ann. of Clin. & Lab. Sci./(1991), 21(4), 275–283.

Blackburn, K. & Highsmith, R. F./Nickel Inhibits Endothelin–Induced Contractions of Vascular Smooth Muscle/Am. J. of Physiol./(1990), 258, C1025–C1030.

Lucassen, M. & Sarkar, B./Nickel (II)—Binding constituents of Human Blood Serum/J. of toxicology & Environmental Health/(1979), 5, 897–905.

Marshall, T. et al/Trace Element Analyses of Diaspirin Cross–Linked Hemoglobin Solutions/Blood Substitutes and Oxygen Carriers/Ed.: T. M. S. Chang/Marcel Dekker, Inc., NY/(1993), 267–270.

Louria, D. B. et al/The Human Toxicity of Certain Trace Elements/Ann. Internal Med./(1972), 76, 307–319.

Fratantoni, J. C./Points to Consider in the Safety Evaluation of Hemoblogin–Based Oxygen Carriers/Transfusion/(1991), 31(4), 369–371.

Gramm, H. J. et al/Spurenelementgehalt in Losungen Zur Parenteralen Ernahrung Und Blutderivaten/Infusionstherapie/(1987), 14, 290–294.

Berner, Y. N. et al/Selected Ultratrace Elements in total Parenteral Nutrition Solutions/Am. J. Clin. Nutr./(1989), 50, 1079–1083.

Leach, C. A. & Sunderman, F. W./Hypernickelemia Following Coronary Arteriography, Caused by Nickel in the Radiographic Contrast Medium/Ann. Clin. & Lab. Sci./(1987), 17(3), 137–144.

Nielsen, F. H./Fluoride, Vanadium, Nickel, Arsenic, and Silicon in Total Parenteral Nutrition/(1984), 60(2), 177–195.

Gross, P. et al/Experimental Asbestosis/The Development of Lung Cancer in Rats with Pulmonary Deposit of Chrysotile Asbestos Dust/Arch. Envir. Health(1967), 15, 343–355.

Koppel, C. & Baudisch, H./Inadvertent Metal Loading of Critically Ill Patients with Acute Renal Failure by Human Albumin Solution Infusion Therapy/Clin. Tox./(1988), 26(5&6), 337–356.

(List continued on next page.)

*Primary Examiner*—Mukund J. Shah
*Assistant Examiner*—Pavanaram K. Sripada
*Attorney, Agent, or Firm*—Henry P. Nowak; Marianne F. Novelli; Theresa A. Brown

[57] ABSTRACT

According to the present invention removal of nickel from a nickel-containing hemoglobin solution is accomplished by exposing the nickel-containing hemoglobin solution to a chelating agent, preferably a multidentate acetic acid based chelator such as EDTA. Methods are provided that allow obtaining essentially nickel-free hemoglobin from nickel-containing hemoglobin solutions, particularly hemoglobin solutions that result from large scale fermentation and/or purification.

30 Claims, 6 Drawing Sheets

OTHER PUBLICATIONS

Holti, G./Immediate and Arthus–Type Hypersensitivity to Nickel/Clin. Allergy/(1974), 4, 437–438.

O'Sullivan, W. J./Stability Constants of Metal Complexes/Data for Biochemical Research/(1969), Oxford University Press, NY, Ed. R. M. C. Dawson, D. C. Elliott, W. H. Elliott, K. M. Jones, Chapter 17, pp. 423–434.

Callan, W. M. & Sunderman, F. W./Species Variations in Binding of $^{63}$NI(II) by Serum Albumin/Res. Comm. Chem. Path. Pharm./(1973), 5(2), 459–471.

Sunderman, F. W./Potential Toxicity from Nickel Contamination of Intravenous Fluids/Ann. of Clin. & Lab. Sci./(1983), 13(1), 1–4.

Fisher, A. A./Nickel—The Ubiquitous Contact Allergen Possible Significance of its Presence in Food, Water, Urine, Hair, and Infusion Fluids/Cur. Contact News/(1978), 22(5), 544–550.

Rubanyi, G. & Balogh, I./Effect of Nickel on Uterine Contraction and Ultrastructure in the Rat/Am. J. Obstet. Gynecol./(1982), 142(8), 1016–1020.

Serda, R. E. & Henzi, M. T./Metal Ion–Binding Properties of Avian Thymic Hormone/The J. of biological Chemistry/(1991), 266(11), 7291–7299.

Sunderman, F. W./A Pilgrimage into the Archives of Nickel Toxicology/Ann. of Clin. & Lab. Sci./(1989), 19(1), 1–16.

Tabata, M. & Sarkar, B./specific Nickel (II)—Transfer Process Between the Native Sequence Peptide Representing the Nickel (II)—Transport Site of Human Serum Albumin and L–Histidine/J. Inorganic Biochem./(1992), 45, 93–104.

Yip, T–T. et al/Evaluation of the Interaction of Peptides with Cu(II), Ni(II), and Zn(II) by High–Performance Immobilized Metal Ion Affinity Chromatography/Anal. Biochem./(1989), 183, 159–171.

Vernon, F./The Preparation and Properties of Chelating Ion Exchange Resins/Chemistry and Industry/(1977), 15, 634–637.

Morgan, W. T./Human Serum Histidine–Rich Glycoprotein/I. Interactions with Heme, Metal Ions and Organic Ligands/Biochim. et Biophys. Acta/(1978), 533, 319–333.

Darnall, D. W. et al/Selective Recovery of Gold and Other Metal Ions from an Algal Biomass/Environ. Sci. Technol./(1986), 20, 206–208.

Edoute, Y. et al/Nickel Chloride Inhibits Metabolic Coronary Vasodilation in isolated Rat Hearts/Federation Proceedings/(1986), 45(3), 1410.

Figura, P. & McDuffie, B./Characterization of the Calcium Form of Chelex–100 for Trace Metal Studies/Analytical Chemistry/(1977), 49(13), 1950–1953.

Rubanyi, G. et al/Nickel is Released from the Ischemic Myocardium and Contracts Coronary Vessels by a Ca–Dependent mechanism/J. Mol. & Cell. Card./(1981), 13, 1023–1026.

Rubanyi, G. & Kovach, A. G. B./Coronary Vasoconstriction Induced by Endogenous Nickel Release in Various Cardiovascular Diseases/Ann. Clin. Lab. Sci./(1981), 11(1), 93.

Oskarsson, A. et al/Effects of Cobalt Chloride, Nickel Chloride, and Nickel Subsulfide and Upon Erythropoiesis in Rats/Ann. of Clin. & Lab Sci./(1981), 11(2), 165–172.

Novelli, E. L. B. et al/Influence of Nickel Chloride on Bone Marrow of Iron–Defiecient Rats/Bol. Estud. Med. Biol. Mex./(1988), 36, 35–42.

Moyers, E. M. & Fritz, J. S./Preparation and Analytical Applications of a Propylenediaminetetraacetic acid Resin/Anal. Chem./(1977), 49(3), 418–423.

Sharma, B. L. et al/Chelation in Metal Intoxication. XIX, α–Mercapto–β–Aryl Acrylic Acid as Antidotes to Nickel and Lead Toxicity/J. of Applied Toxicology/(1986)/6(4) 253–257.

Haner et al. Archives Biochem and Biophys vol. 231 No. 2., pp. 477–486., 1984.

Sunderman., Annals of Clinical and Lab. Sciences., vol. 13, No 1., 1983.

Moi et al. Anal. Biochem., 148., pp. 249–253. (1985).

EDTA Wash of the U/F System
(3/18/93)

NICKEL-FREE HEMOGLOBIN AND METHODS FOR PRODUCING SUCH HEMOGLOBIN

This invention relates to hemoglobin solutions that are essentially free of nickel contamination and to methods of obtaining such nickel-free hemoglobin solutions.

BACKGROUND

Trace amounts of most metals, including nickel, are required for adequate human health. However, excesses of these metals can result in toxic effects. The toxicological effects of nickel to mammals and particularly to humans has been documented since the middle of the fifteenth century when German miners were noted to have high levels of lung disorders (Sunderman, (1989) Annals of Clin. Lab. Science 19(1): 1–16). Beginning in 1884 with T. P. Anderson Stuart, systematic studies have been conducted on the toxicology of nickel so that excessive nickel is now recognized as a major contributing factor to many mammalian disorders. For example, nickel poisoning has been implicated in pneumonitis with adrenal cortical insufficiency, abnormal hyaline membrane formation, pulmonary edema and hemorrhage, hepatic degeneration, brain and renal congestion, cancer of the respiratory tract, pulmonary eosinophilia, asthma, primary irritant dermatitis, allergic dermatitis urticaria, eczema, allergenic reactions, osteomyelitis, osteonecrosis, etc. (Sunderman, (1989) Annals of Clin. Lab. Science 19(1): 1–16; Louria et al., (1972) Annals of Internal Medicine 76:307– 319). In addition, nickel has been hypothesized to increase vasoconstriction during myocardial infarction (Rubanyi et al., (1981) J. Mol. Cellular Cardiology 13:1023–1026; Rubanyi et al., (1981) Ann. Clin. Lab. Sci. 11(1):93) and to stimulate the contraction of smooth muscle (Rubanyi and Balogh, (1982) Am J. Obstet. Gynecol. 142:1016–1020). Nickel, which is a component of asbestos, has been suggested as the tumor inducing component of asbestos (Louria et al., (1972) Annals of Internal Medicine 76:307–319; Gross et al., (1967) Environ. Health 15:343–355). Numerous investigators have studied the toxicological effects of nickel including Holti, (1974)Clin. Allergy 4:437–438; Novelli et al., (1988) Bol. Estud. Med Biol., Mex. 36:35–42; Knight et al., (1987) Ann. Clin. Lab. Sci. 17(4) 275; Edoute et al., (1986) Federation Proceedings 45(3): 1410; Leach et al., (1984) Ann. Clin. Lab. Sci. 14(5): 414–415; Oskarsson et al., (1981) Ann. Clin. Lab. Sci. 11(2):165–172; Blackburn and Highsmith, (1990) Am. J. Physiol. 258:C1025–C1030; Knight et al., (1991) Ann. Clin. Lab. Sci. 21(4):275–283; Sarkar, (1984) in *Nickel in The Human Environment,* International Agency for Research on Cancer, Lyon, France; and Kilburn et al., (1990) Am. J. Indust. Med. 17:607–615.

Nickel poisoning can result from direct contact with nickel containing metal objects such as needles (Sunderman, (1983) Ann. Clin. Lab. Sci. 13(1):1–4) or by contact with solutions containing dissolved nickel (Fisher, (1978) Current Contact News 22(5):544–550). The solutions where nickel poisoning can be a potential hazard are for the most part large volume body solutions. Such solutions include dialysis solutions (Sunderman, (1983) Ann. Clin. Lab. Sci. 13(1):1–4), human albumin solutions (Sunderman, (1983) Ann. Clin. Lab. Sci. 13(1):14; Koppel et al., (1988) Clin. Tox. 26:337–356; Tabata and Sarkar, (1992) J. Inorg. Chem. 45:93–104; Lucassen and Sarkar, (1979) J. Tox. Env. Health 5:897–905; Morgan, (1978) Biochimica Biophysica Acta 533:319–333; Callan and Sunderman, (1973) Res. Comm. Chem. Path. Pharm. 5(2):459–472), radiographic contrast medium (Leach and Sunderman, (1987) Ann. Clin. Lab. Sci. 17(3):137–144; Leach and Sunderman, (1986) Ann. Clin. Lab. Sci. 16(4):327–328), and total parenteral nutrition solutions (Berner et al., (1989) Am. J. Clin. Nutr. 50:1079–1083; Gramm et al., (1987) Infusiontherapie 14:290–294; Nielsen, (1984) Bull. N.Y. Acad. Med. 60(2)177–195) and blood products (Gramm et al., (1987) Infusiontherapie 14:290–294; Center for Biological Evaluation and Research, (1991) Transfusion 31(4): 369–371). Marshall et al. ((1993) in *Blood Substitutes and Oxygen Carriers,* Chang ed., Marcel Dekker, Inc., New York, pp. 267–270) conducted a trace element analysis of diaspirin cross-linked hemoglobin solutions, measuring the levels of 23 trace metals. They concluded that calcium, magnesium, zinc and iron were the only elements present at high enough levels to be detected, while 19 other metals could not be detected (Note that 24 metals were said to be measured, but results are only shown for 23).

The source of nickel contamination in large volume body solutions may originate from metals present in the starting materials and from process contamination (Marshall et al., (1993) in *Blood Substitutes and Oxygen Carriers,* Chang ed., Marcel Dekker, Inc., New York, pp. 267–270). There is evidence that leaching from stainless steel equipment increases the nickel content of solutions that come in contact with such equipment (Sunderman, (1983) Ann. Clin. Lab. Sci. 13(1):1–4). Some nickel can be airborne or in water sources allowing contamination of starting materials. For example, albumin has a high affinity for nickel so that any material using albumin is likely to contain some nickel (Sarkar, (1984) in *Nickel in The Human Environment,* International Agency for Research on Cancer, Lyon, France).

There are methods available for attempting to remove nickel from various solutions, but the success of a particular method for a particular solution is unpredictable. For example, various chelating resins have been used to separate various metals from a solution, including nickel, although many times such separation is effective at very low pH making it potentially damaging to proteins (e.g., hemoglobin) that may be in the solution (Figura and McDuffie, (1977) Anal. Chem. 49:1950–1953; Darnall et al., (1986) Envir. Sci. Tech. 20:206–208; Vernon, (1977) Chem. and Industry 15:634–637; Moyers and Fritz, (1977) Anal. Chem. 49:418–423; yip et al., (1989) Anal. Biochem. 183:159–171; U.S. Pat. No. 4,952,684; see Example 3).

Ethylenedinitrilo tetraacetate (EDTA) has been used as a chelating agent, but until the present invention it has not been used alone in solution to remove nickel from a protein solution containing nickel. EDTA has been used as a ligand in derivatized agarose chromatography to remove calcium (Serda and Henzel, (1991) J. Biol. Chem. 266:7291–7299) and it has been used as part of an affinity labelled chelating complex to introduce a probe into a protein or nucleotide system or as a gel to remove calcium and lanthanide ions from the binding protein parvalbumin (Haner et al., (1984) Archives Biochem. Biophys. 231:477–486; Haner et al., (1984) Anal. Biochem. 138:229–234). EDTA has also been observed to inhibit the binding of cadmium, copper, lead and zinc to Ca-Chelex chelating columns (Figura and McDuffie, (1977) Anal. Chem. 49:1950–1953).

SUMMARY OF THE INVENTION

The present invention relates to the production of nickel-free hemoglobin. Removal of nickel from a nickel-containing hemoglobin solution is accomplished by exposing the nickel-containing hemoglobin solution to a chelating agent, preferably a multidentate acetic acid based chelator, more preferably ethylenedinitrilo tetraacetate (EDTA), [[(carboxymethyl)imino]bis(ethylenedinitrilo)]tetraacetate (DPTA), triethylenetetraaminehexaacetate (TTHA), ethylene glycol-bis(2-aminoethyl ether-N,N,N',N'-tetraacetic acid (EGTA), most preferably EDTA.

A preferred method of exposing the nickel-containing hemoglobin solution to a chelating agent is by diafiltration with at least 5 turnover volumes of a chelating agent solution, more preferably at least 5 turnover volumes. Preferably, the chelating agent solution is at least 1 mM, more preferably from about 5 to about 10 mM in chelating agent.

In a preferred embodiment of the present invention, exposing a nickel-containing hemoglobin solution to a chelating agent occurs for a period of time sufficient to remove at least 80 percent, preferably 90 percent, more preferably 95 percent of the nickel from the nickel-containing hemoglobin solution.

In another preferred embodiment of the present invention, removal of the chelating agent is by diafiltration with formulation buffer, more preferably a formulation buffer that is a chelating agent solution minus chelating agent.

In another preferred embodiment of the present invention, a nickel-containing hemoglobin solution is obtained by a large scale fermentation and/or purification process, more preferably hemoglobin selected from the group consisting of recombinant hemoglobin and mutant hemoglobin.

In a very preferred embodiment of the present invention, a method for obtaining essentially nickel-free hemoglobin comprises removal of nickel from a nickel-containing hemoglobin solution by diafiltering the nickel-containing hemoglobin solution with at least 10 turnover volumes of at least 10 mM EDTA in a formulation buffer for sufficient time to allow chelating of at least 90 percent of nickel in the nickel-containing hemoglobin solution, followed by removal of the chelating agent by diafiltering with formulation buffer.

The present invention also contemplates essentially nickel-free hemoglobin obtained according to the methods of this invention as well as pharmaceutical compositions containing such essentially nickel-free hemoglobin.

The present invention also contemplates a method for preventing symptoms of nickel toxicity in a mammal associated with administration of nickel-containing hemoglobin comprising administration to said mammal a pharmaceutical composition comprising essentially nickel-free hemoglobin according to the present invention.

DETAILED DESCRIPTION OF THE INVENTION

Figure 1:
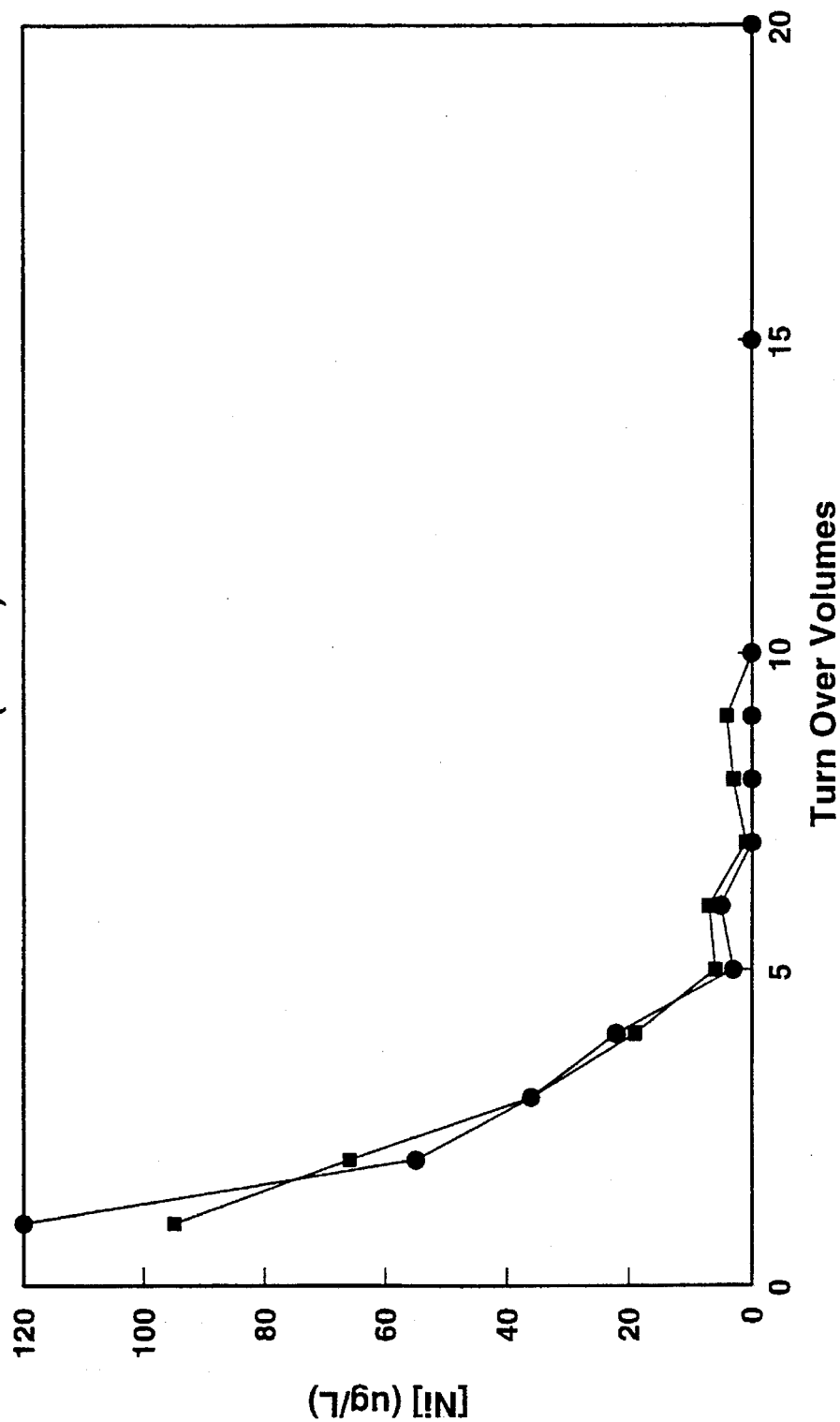
FIG. 1 shows [$Ni^{2+}$] of the retentate (■) and the permeate (●) of Run 1. The retentate [$Ni^{2+}$] and the permeate [$Ni^{2+}$] were nearly equal throughout the run. The nickel was reduced to nondetectable levels (i.e., $\leq 1$ µg/L) by the tenth TOV. The final concentrate was found to contain 21 µg/L (ppb) in a 41.6 gm hemoglobin solution. The [$Ni^{2+}$]/Hb ratio was 0.5 µg/mg.

The present invention relates to the production of nickel-free hemoglobin. Removal of nickel from a nickel-containing hemoglobin solution is accomplished by exposing the nickel-containing hemoglobin solution to a chelating agent, preferably a multidentate acetic acid based chelator for sufficient time to allow chelating of significant nickel, followed by removal of the chelating agent. Usually, although not a requirement, the nickel-containing hemoglobin solution has undergone initial purification to remove non-hemoglobin proteins and other cellular and serum contaminants prior to removal of the nickel.

Utilizing the method of the present invention allows removal of nickel from nickel-containing hemoglobin solutions. This method is useful to remove nickel from any nickel-containing hemoglobin solution. A nickel-containing hemoglobin solution is a hemoglobin solution wherein [$Ni^{2+}$] $\geq 20$ µg/L or $Ni^{2+}$/Hb $\geq 0.4$ µg/gm.

Nickel-containing hemoglobin solutions may often be found in any hemoglobin solution that has been exposed to stainless steel or other nickel-containing metal alloy during any part of its production (e.g., fermentation) or purification process, particularly any large scale fermentation and/or purification of hemoglobin where stainless steel components are used. Large scale fermentation and/or purification of hemoglobin is any fermentation and/or purification process that either utilizes large solution volumes or utilizes stainless steel components at any point in the fermentation/purification process such that the stainless steel components come in contact with the hemoglobin solution during the process. Typically, large scale fermentation and/or purification occurs when either fermentation or purification involve handling of cell cultures or hemoglobin solutions of at least 5 liters, preferably at least 15 liters, more preferably at least 500 liters, most preferably at least 1000 liters.

Another source of nickel in nickel-containing hemoglobin solutions is reagents containing trace amounts of nickel. Although nickel quantities in many reagents for buffers, salts, etc. are very low, when large scale fermentation and/or purification takes place, significant nickel can result in nickel-containing hemoglobin solutions. This is because even small amounts of nickel are "harnessed" by hemoglobin, which has a high affinity for nickel.

SOURCES OF HEMOGLOBIN

For the purpose of the appended claims, a "hemoglobin" or "hemoglobin-like protein" comprises one or more heterotetramers composed of (a) two alpha globin-like and two beta globin-like polypeptides, (b) one di-alpha globin-like and two beta globin-like polypeptides, (c) two alpha globin-like and one di-beta globin-like polypeptides, (d) one di-alpha globin-like and one di-beta globin-like polypeptides, (e) one fused alpha/beta globin-like polypeptide and separate alpha and beta globin-like polypeptides, or (f) two fused alpha/beta globin-like polypeptides. A polypeptide of one tetramer may be crosslinked or genetically fused to a polypeptide of another tetramer. A hemoglobin is said to be multimeric if it comprises more than four globin subunits or domains. The term "multimeric" thereby includes octameric hemoglobin (2 linked tetramers), as well as higher multimers. Preferably, the hemoglobin has the ability to bind oxygen with one or more heme prosthetic groups.

A human alpha globin-like domain or polypeptide is native human alpha globin or a mutant thereof differing from the native sequence by one or more substitutions, deletions or insertions, while remaining substantially homologous (as hereafter defined) with human alpha globin, and still capable of associating with beta globin. A beta globin-like domain or polypeptide is analogously defined. Subunits of animal hemoglobins or mutants thereof which are sufficiently homologous with human alpha or beta globin are embraced by the term "human alpha or beta globin-like domain or polypeptide." For example, the subunits of bovine hemoglobin are within the scope of these terms. The alpha- and beta- globin-like polypeptides may be referred to collectively as "globins". For the sake of convenience the term "polypeptide" may refer to a unitary chain or to a domain of a longer polypeptide chain. Preferably, the globin-like domain or polypeptide has the ability to incorporate heme.

A "genetically fused hemoglobin" is a hemoglobin-like protein comprising at least one "genetically fused globin-like polypeptide" (globin pseudooligomer), the latter comprising two or more globin-like domains which may be the same or different. A di-alpha globin-like polypeptide is one which consists essentially of two alpha-globin-like polypeptide sequences (domains) connected by peptide bonds between the normal C-terminus of the first alpha-globin-like polypeptide (domain) and the normal N-terminus of the second alpha-globin-like polypeptide (domain). These two sequences may be directly connected, or connected through a peptide linker of one or more amino acids; the term "peptide bonds" is intended to embrace both possibilities. Alpha globin chains crosslinked at the N- and C-terminals other than by peptide bonds (e.g., by DIDS, diisothiocyanostilbene-2,2'-disulfonate; Kavanaugh et al., (1988) Biochemistry 27:1804–1808) are not di-alpha globins. The di-alpha globin-like polypeptide preferably is capable of folding together with beta globin and incorporating heme to form functional hemoglobin- like protein. The di-beta globin-like polypeptide is analogously defined. A di-alpha or di-beta globin-like polypeptide with a mutation in only one of the component domains is called "asymmetric".

It is also possible to provide an "alpha/beta-globin- like pseudodimer" in which an alpha globin-like sequence is connected by peptide bonds to a beta globin-like sequence. This "alpha/beta globin-like polypeptide", and the di-alpha and di-beta globin-like polypeptides, may collectively be referred to as "pseudodimeric globin-like polypeptides" or as "diglobins". By extension, a hemoglobin-like protein comprising a di-alpha, a di- beta, or a alpha/beta globin-like polypeptide is a "pseudotetramer".

Even though the di-alpha hemoglobin does not dissociate into dimers, it is still cleared from the bloodstream, albeit more slowly than is the case for normal hemoglobin.

In determining whether a polypeptide is substantially homologous to alpha (or beta) globin, sequence similarity is an important but not exclusive criterion. Sequence similarity may be determined by conventional algorithms, which typically allow introduction of a small number of gaps in order to achieve the best fit. Preferably, the alpha-globin-like polypeptides (or domains thereof) of the present invention have at least about 75% sequence identity with wild-type human alpha globin. However, a polypeptide of lesser sequence identity may still be considered "substantially homologous" with alpha globin if it has a greater sequence identity than would be expected from chance and also has the characteristic higher structure of alpha globin and similar biological activity. By way of comparison, Artemia's heme-binding domains are considered homologous with myoglobin even though the primary sequence similarity is no more than 27%, as alignment of the heme- binding domains around their conserved residues and the residues conserved in other hemoglobins (i.e., involved in heme contacts or in determining the relationship of the helical segments to each other) suggested that the Artemia domains possessed the classical globin helices A to H with their corresponding turns, as well as various conserved globin family residues. Also, among the serine protease inhibitors, there are families of proteins recognized to be homologous in which there are pairs of members with as little as 30% sequence homology.

Well over a hundred mutants of human hemoglobin are known, affecting both the alpha and beta chains, and the effect of many of these mutations on oxygen-binding and other characteristics of hemoglobin are known. The human alpha and beta globins themselves differ at 84 positions. In addition, interspecies variations in globin sequence have been extensively studied. Dickerson, *Hemoglobin Structure, Function, Evolution and Pathology* ch. 3 (1983) reported that in 1982, the 60 known vertebrate alpha globins had identical residues at 23 of their 141 positions, while for the 66 vertebrate beta globins considered, 20 of the 146 amino acids are identical. The 60 vertebrate myoglobins, which also belong to the globin family, had 27 invariant amino acids out of 153 positions. If only mammals are considered, then the invariant amino acids are 50/141 for the alpha globins, 51/146 for the beta globins, and 71/153 for the myoglobins. Invariant positions cluster around the centers of activity of the molecule: the heme crevice and the intersubunit contacts. Of the variable amino acids, some diverge from the consensus sequence for only a small fraction of the species considered.

The number of total differences between human alpha globin and selected other vertebrate alpha globins is as follows: rhesus monkey (4), cow (17), platypus (39), chicken (35), human zeta (embryonic) (61), carp (71), and shark (88). For invertebrate globins the divergences are sea lamprey (113), mollusc (124), Glycera (marine bloodworm) (124) and Chironomus (midge) (131). Turning to the beta globin family, the differences of human beta globin from other vertebrate beta globins are rhesus monkey (8), human delta globin (10), cow beta globin (25), cow gamma globin (33), human gamma globin (39), human epsilon (embryonic) globin (36), platypus (34), chicken (45), shark (96), sea lamprey (123), mollusc (127), Glycera (125) and Chironomus (128).

Many of these differences may be misleading—variable amino acids may exhibit only "conservative substitutions" of one amino acid for another, functionally equivalent one. A "conservative substitution" is a substitution which does not abolish the ability of a globin-like polypeptide (or domain) to incorporate heme and to associate with alpha and beta globin subunits to form a tetrameric (or pseudotetrameric) hemoglobin- like protein, which preferably will reversibly bind oxygen. The following resources may be used to identify conservative substitutions (and deletions or insertions):

(a) data on hemoglobin mutants (over a hundred such mutants exist);

(b) data on sequence variations among vertebrate, especially mammalian, alpha globins and beta globins;

(c) data on sequence variations among vertebrate, especially mammalian, myoglobins;

(d) data on sequence variations between vertebrate and invertebrate globins, or among the invertebrate globins;

(e) data on the three-dimensional structures of human hemoglobin and other substantially homologous proteins, and molecular modeling software for predicting the effect of sequence changes on such structures; and (f) data on the frequencies of amino acid changes between members of families of homologous proteins (not limited to the globin family). See, e.g., Table 1–2 of Schulz and Schirmer, *Principles of Protein Structure* (Springer- Verlag: 1979) and FIGS. 3–9 of Creighton, *Proteins Structure and Molecular Properties* (W. H. Freeman: 1983).

While the data from (a)–(d) is most useful in determining tolerable mutations at the site of variation in the cognate proteins, it may also be helpful in identifying tolerable mutations at analogous sites elsewhere in the molecule. Based on the data in category (f), the following exchange groups may be identified, within which substitutions of amino acids are frequently conservative I. small aliphatic, nonpolar or slightly polar residues— Ala, Ser, Thr (Pro, Gly)

II. negatively charged residues and their amides—Asn Asp Glu Gln

III. positively charged residues—His Arg Lys

IV. large aliphatic nonpolar residues—Met Leu Ile Val (Cys)

V. large aromatic residues—Phe Tyr Trp

Three residues are parenthesized because of their special roles in protein architecture. Gly is the only residue without a side chain and therefore imparts flexibility to the chain. Pro has an unusual geometry which tightly constrains the chain. Cys can participate in disulfide bonds which hold proteins into a particular folding. Note that Schulz and Schirmer would merge I and II above. Note also that Tyr, because of its hydrogen bonding potential, has some kinship with Ser, Thr, etc.

In general, functionality (i.e., oxygen binding capability), which is preferred but not required, is less likely to be affected by mutations at surface residues, at least those not involved in either the heme crevice or the subunit contacts. In addition, "loops" connecting alpha helices, especially the D loop of the alpha helix, as well as free amino or carboxy termini, are more tolerant of deletions and insertions.

Hemoglobin is readily available from a number of sources. Slaughter houses produce very large quantities of hemoglobin in the form of blood which is currently usually sold as an inexpensive fertilizer. If particular species or breed of animal produces a hemoglobin especially suitable for a particular use, those creatures may be specifically bred for this purpose, in order to supply the needed blood. Also, transgenic animals may be produced that can express a mutant hemoglobin. Human blood banks must discard human blood after a certain expiration date. This also produces large quantities of hemoglobin.

In addition to extraction from animal sources, the genes encoding subunits of a desired hemoglobin may be cloned, placed in a suitable expression vector and inserted into an organism, such as a microorganism, animal or plant, or into cultured animal or plant cells or tissues. These organisms may be produced using standard recombinant DNA techniques. Human alpha and beta globin genes have been cloned and sequenced by Liebhaber et al., *Proc. Natl. Acad. Sci.* USA 77;7053–7058 (1980) and Marotta et al., *Journal of Biological Chemistry,* 252; 5040–5053 (1977) respectively. Techniques for expression of both wild-type and mutant alpha and beta globins, and their assembly into a hemoglobin, are set forth in U.S. Pat. No. 5,028,588 and PCT/US90/02654, PCT/US91/09624, and European Patent Application 87116556.9.

Hemoglobin Ao is a heterotetramer composed of two alpha globin subunits ($\alpha 1, \alpha 2$) and two beta globin subunits ($\beta 1, \beta 2$). There is no sequence difference between $\alpha 1$ and $\alpha 2$ or $\beta 1$ and $\beta 2$. In the unoxygenated ("deoxy", or "T" for "tense") state, the subunits form a tetrahedron. The $\alpha 1 \beta 1$ and $\alpha 2 \beta 2$ interfaces remain relatively fixed during oxygen binding, while there is considerable flux at the $\alpha 1 \beta 2$ and $\alpha 2 \beta 1$ interfaces. In the oxygenated ("oxy" or "R" or relaxed) state, the intersubunit distances are increased. The subunits are noncovalently associated by Van der Waals forces, hydrogen bonds and, for deoxy Hgb, salt bridges. Hemoglobin is known to dissociate into $\alpha 1 \beta 1$ and $\alpha 2 \beta 2$ dimers, which are eliminated from the bloodstream by renal filtration. Intravascular retention of hemoglobin has been improved by, e.g., chemical crosslinking of subunits of a single tetramer, or between tetramers.

As taught in U.S. Pat. No. 5,028,588, WO 90/13645, published Nov. 15, 1990, and U.S. patent application Ser. No. 789,179 filed Nov. 8, 1991, it is possible to produce a pseudotetrameric hemoglobin in which two noncovalently associated subunits are replaced by a single pseudodimeric polypeptide with two oxygen binding domains, joined either directly or by a linker of one or more amino acids. This pseudodimeric polypeptide may be expressed from a suitable fused gene. Thus, two alpha globin genes may be fused into a "di-alpha globin" gene, or two beta globin genes into a "di-beta globin" gene, or alpha and beta globin genes into an "alpha beta" globin pseudodimer gene.

The advantage of fusing two or more globin chains together is that one can selectively mutate one but not both of the chains, as taught in U.S. patent application Ser. No. 789,179 filed Nov. 8, 1991. This permits one to provide only one attachment site for the drug of interest so that equimolar amounts of drug and hemoglobin are found in the final product. This also permits creation of an octamer through selective mutation of an amino acid to a cysteine in one of the chains to provide a site for a disulfide linkage.

Another alternative is to have numerous attachment sites on the hemoglobin molecule. This would permit stabilization of higher amounts of the chemical being bound, and would provide the potential for encompassing different release rates of drug bound to one hemoglobin.

Hemoglobin isolated from natural sources has been chemically modified using many techniques in the past. Any of these techniques may be used to prepare hemoglobin. Examples of such modifications are found in U.S. Pat. Nos. 4,412,989, 4,301,144, 4,670,417, 4,321,259, 4,473,563, 4,710,488, 4,650,786, 4,336,248, 4,598,064, 4,600,531 and 4,377,512 among others.

Individual globin chains have been reassorted with modified forms to synthesize a semi-synthetic hemoglobin as well (Luisi et al., *Nature* 320; 555–556 (1986) and Nagai et al., *Nature* 329; 858–860 (1987)). Other modifications such as chemical polymerization of globin chains, glycosylation, pegylation, encapsulation in a liposome or cell membranes are also contemplated.

The hemoglobin produced by expression of recombinant DNA also lends itself to easy modification. By applying the standard techniques of site specific mutagenesis to the globin gene(s), (McCracken et al., Biotechniques 6; 338–339 (1988) and Zoller et al., *Methods in Enzymology* 100; 468–500 (1987) are recent examples) one can add, subtract or change any amino add or combination of amino acids in the resulting globin chain. The modified portions may constitute an attachment site for the drug of interest. This may alter the number and locations where the drug is associated with or binds to the hemoglobin molecule. If the drug of interest is itself a polypeptide, one may add it onto the globin chain to yield a drug-hemoglobin conjugate.

Chemically crosslinked hemoglobins (WO 92/11283, published Jul. 9, 1992; U.S. Pat. No. 4,857,636; U.S. Pat. No. 5,194,590; U.S. Pat. No. 5,084,558), or mutant hemoglobins which genetically fuse the alpha subunits (di-alpha Hgb) or the beta subunits (di-beta Hgb), may increase intravascular retention by inhibiting haptoglobin binding.

Any of the hemoglobins or fragments thereof may be modified to alter the biological activity of the hemoglobin itself. For example, U.S. Pat. Nos. 5,028,588 and 5,173,426 teach use of low oxygen affinity mutants as blood substitutes. Such a modified molecule may also be conjugated to a drug to form a drug-hemoglobin conjugate which is contemplated by the invention.

Preferred hemoglobins are SGE1.1 as well as a mutant (alpha D75C) of the known pseudotetramer SGE1.1 and alpha Lys 16 Cys as described in WO 90/13645, published Nov. 15, 1990, and U.S. patent application Ser. No. 789,179 filed Nov. 8, 1991.

INITIAL PURIFICATION

Purification of hemoglobins can be accomplished by a variety of methods. Generally, a combination of chromatography, heating, filtration, cell disruption and buffer exchange are used. For example, Estep (U.S. Pat. Nos. 4,831,012 and 4,861,867) and Sehgal et al., (U.S. Pat. No. 5,194,590) have described purification of hemoglobin from outdated human red blood cells. Rausch et al., (U.S. Pat. No. 5,084,558) has described purification of hemoglobin from bovine blood. Chang (WO 87/00177) has described the purification of hemoglobin from stroma free blood solutions. Hoffman et al. (U.S. Pat. No. 5,028,588, WO 90/13645, published Nov. 15, 1990, and U.S. patent application Ser. No. 789,179 filed Nov. 8, 1991) describe the isolation of recombinant hemoglobin from *E. coli* fermentation cell cultures. Any of the published or standard techniques may be used.

REMOVAL OF NICKEL

Nickel removal from hemoglobin solutions can be accomplished at any time in the initial purification process, although preferably, the nickel removal step occurs at or near the end of the initial purification process. It is often convenient for the nickel removal to occur after chromatography and before final finish and fill (aseptic fill) of the purified hemoglobin solution.

Removal of nickel from a nickel-containing hemoglobin solution is accomplished by exposing the nickel-containing hemoglobin solution to a chelating agent, preferably a multidentate acetic acid based chelator for sufficient time to allow chelating of significant nickel, followed by removal of the chelating agent. Preferably the exposure and removal of the chelating agent is by titration of the chelating agent into the effluent of a chromatography column during initial purification, diafiltration, ultrafiltration, or dialysis. The most preferred method for removal is diafiltration.

Typically, a concentrated nickel-containing hemoglobin solution can be diafiltered with 1–40, preferably 5–10 turnover volumes (TOV) of a chelating agent solution. Suitable chelating agent solutions, preferably multidentate acetic acid chelator solutions, most preferably EDTA, are at least 1 mM, preferably 5–10 mM. The chelating agent, including those chelated to the nickel, can then be removed by diafiltration with a formulation buffer (1–40, preferably 5–10 turnover volumes), preferably, the chelating agent solution without the chelating agent present. Turnover volume is the amount of formulation buffer initially utilized in the diafiltration process prior to addition of a chelating agent solution; it is the initial volume of solution to be diafiltered. Therefore, if 10 liters of hemoglobin solution are diafiltered against 4 TOV of chelating agent solution, the 10 liters of nickel-containing hemoglobin solution is diafiltered with 40 liters of chelating agent solution. Besides diafiltration with a chelating agent solution, the nickel-containing hemoglobin solution can be exposed to the chelating agent by titrating a nickel-containing hemoglobin solution with a chelating agent solution until the nickel-containing hemoglobin solution has a suitable amount of chelating agent. The chelating agent can then be removed in the same way as above by diafiltering with a formulation buffer.

Chelating agents include those known in the art (e.g., Sullivan, (1969) "Stability Constants of Metal Complexes," in *Data for Biochemical Research,* Dawson et al. (editors) Oxford University Press, New York, pp. 424–429), preferably multidentate acetic acid chelators, more preferably (ethylenedinitrilo) tetraacetate (EDTA), [[(carboxymethyl) imino]-bis(ethylenedinitrilo)]tetraacetate (DPTA), triethylenetetraaminehexaacetate (TTHA), ethylene glycol-bis(2-aminoethyl ether-N,N,N',N'-tetraactetic acid (EGTA), most preferably EDTA.

Length of exposure of the nickel-containing hemoglobin solution to the chelating agent is typically long enough to allow chelating of significant nickel. Chelating of significant nickel means that at least 80 percent, preferably at least 90 percent, more preferably at least 95 percent of the nickel in the nickel-containing hemoglobin solution is chelated. Chelating and removal of a significant amount of nickel from a nickel-containing hemoglobin solution results in purified essentially nickel-free hemoglobin. Most preferably, a purified essentially nickel-free hemoglobin solution will have [$Ni^{2+}$]<20 μg/L and $Ni^{2+}$/Hb<0.4 μg/gm.

A suitable amount of chelating agent to which the nickel-containing hemoglobin solution is exposed will be at least stoichiometrically equivalent to the amount of nickel in the nickel-containing hemoglobin solution. To assure rapid and efficient removal of significant amounts of nickel from the nickel-containing hemoglobin solution, the amount of chelating agent will preferably be in excess by at least 100 fold, more preferably in excess by at least 1000 fold, most preferably in excess by at least 2500 fold.

A typical and convenient procedure for removing nickel from nickel-containing hemoglobin solutions is as follows. Following elution from the final chromatography column, the nickel-containing hemoglobin solution can be concentrated over an ultrafiltration membrane to a suitable volume. Then, it can be diafiltered with 1–40, preferably 5–10 turnover volumes (TOV) of a suitable formulation buffer (e.g., 5 mM NaPi/150 mM NaCl, pH 7.4) supplemented with a chelating agent, preferably EDTA, to at least 1 mM, preferably 5–10 mM, most preferably 10 mM. Next, the hemoglobin solution can be diafiltered with formulation buffer without chelating agent to remove the chelating agent. Finally, the hemoglobin solution can be further concentrated. Measurement of [$Ni^{2+}$] can be obtained by atomic absorption of both the permeate (buffer washed through the ultrafiltration membrane) and the retentate (the hemoglobin-containing solution that does not permeate the membrane).

The following measurements can be performed on each batch of bulk:

1. color/appearance
2. P50
3. Hill coefficient
4. tryptic mapping
5. total hemoglobin
6. pH
7. high performance size exclusion chromatography (HPSEC)
8. percent methemoglobin
9. metals concentration by atomic absorption
10. chelating agent concentration

PHARMACEUTICAL COMPOSITIONS

The essentially nickel-free hemoglobin described herein may be used in pharmaceutical compositions as an oxygen carrier or as a drug delivery vehicle. In particular, they may be used as a method for preventing symptoms of nickel toxicity in a mammal associated with administration of nickel-containing hemoglobin comprising administration to said mammal a pharmaceutical composition comprising essentially nickel-free hemoglobin according to the present invention.

The present invention provides for such pharmaceutical compositions and formulations for use in delivery of oxygen to tissues, hypoxic tissues, and cell cultures, for stimulation of erythropoiesis, treatment of anemia, and as a drug delivery vehicle for other drugs. The compositions of the invention can be incorporated in conventional solid or liquid pharmaceutical formulations (e.g. tablets, capsules, caplets, injectable or orally administrable solutions) for use in treating mammals in need thereof. The pharmaceutical formulations of the invention comprise a physiologically and/or pharmaceutically effective amount of the essentially nickel-free hemoglobin of the present invention as the active ingredients alone or in combination with other active or inert agents. For example, a parenteral therapeutic composition may comprise a sterile isotonic saline solution containing between 0.1 percent and 90 percent of hemoglobin. The quantity of pharmaceutical provided to the individual is sufficient to provide a blood concentration of between 0.0001 micromolar and 0.005 micromolar of essentially nickel-free hemoglobin. It will be appreciated that the unit content of active ingredients contained in an individual dose of each dosage form need not in itself constitute an effective amount since the necessary effective amount can be reached by administration of a plurality of capsules, tablets, injections, etc. or combinations thereof.

Each formulation according to the present invention may additionally comprise inert constituents including pharmaceutically-acceptable carriers, diluents, fillers, salts, and other materials well-known in the art, the selection of which depends upon the dosage form utilized, the condition being treated, the particular purpose to be achieved according to the determination of the ordinarily skilled artisan in the field and the properties of such additives.

The pharmaceutical compositions of the invention may be administered to an individual by any conventional means such as orally, by aerosol, by transdermal adsorption, by adsorption through a mucus membrane or by injection. Parenteral administration is preferred, particularly intravenously or intraarterial.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

All references cited herein are hereby incorporated by reference for their relevant teachings.

EXAMPLES

The following examples are provided by way of describing specific embodiments of the present invention without intending to limit the scope of the invention in any way.

Example 1

Fermentation of Recombinant Hemoglobin in *E. coli*

The two liter fermentation procedures described below were used to obtain material for purification and functionality determinations.

The seed stock was *E. coli* strain JM109 transformed with the plasmid (pSGE1.1-E4) described in WO 90/13645, published Nov. 15, 1990, and U.S. patent application Ser. No. 789,179 filed Nov. 8, 1991. The plasmid contains a gene that expresses human hemoglobin with two significant modifications. First, beta asparagine 108 has been changed to lysine. Second, a di-alpha globin has been produced using a glycine to connect the amino terminus of one alpha chain to the carboxy terminus of the other alpha chain. These mutations produce a preferred hemoglobin that has an increased half life and advantageous oxygen binding characteristics.

To prepare the fermenter inoculum, 400 µl of seed stock were inoculated into 200 mL of 4.1 g/L $KH_2PO_4$, 7.0 g/L $KHPO_4$, 2.0 g/L $(NH_4)_2SO_4$, 1.0 g/L $Na_3$ Citrate. $2H_2O$, 154 mg/L $MgSO_4.7H_2O$, up to 230 mg of proline, 0.2% yeast extract, 1% glucose, 300 µl of 20 mg/ml thiamine in sterile-filtered solution, 133 µl of 15 mg/ml tetracycline, and 0.6 ml of a trace metal solution. The trace metal solution contained 25 µg/ml $FeCl_3+6H_2O$, 1.3 µg/ml $ZnCl_2$, 2.0 µg/ml $CaCl_2.6H_2O$, 2 µg/ml $Na_2MoO_4.2H_2O$, 2.54 µg/ml $Cu(II)SO_4.5H_2O$, 0.5 µg/ml $H_3BO_3$, 1.2 µg/ml $MnCL_2.4H_2O$, and 100 µl/ml HCl dissolved in a 0.5M Na-citrate solution. This culture was allowed to grow at 37° C. on a shaker until an $O.D._{600nm}$ of 0.4–0.6 was achieved. The entire inoculum was then aseptically transferred to a 2-liter fermentor containing 2 g/L $KH_2PO_4$, 3.6 g/L $KHPO_4$, 2.0 g/L $(NH_4)_2SO_4$, 1 mL/L polypropylene glycol-2000, 50 mL/L of 50% glucose, 100 mg/L of thiamine, 9.75 mg/L of tetracycline, 4 mL/L of trace metals, 1.54 g/L $MgSO_4.7H_2O$ and 3.68 g/L $Na_3$ Citrate. $2H_2O$. The pH was maintained at 6.8 by addition of 15% to 30% $NH_4OH$, dissolved oxygen was maintained at or above 30%, and 60% glucose is added throughout the growth period, sufficient to maintain low but adequate levels of glucose in the culture (0.5 g/L–10 g/L). The culture was grown between 25° and 30° C. to an $OD_{600}$~10–40 prior to induction with 10–1000 µM IPTG, preferably 30 µM IPTG. Upon induction of hemoglobin synthesis, the E. Coli heme biosynthesis was supplemented by addition of hemin, either by addition of the total mass of hemin required at induction, or by periodic addition of hemin dissolved in 50 mM to 1M NaOH (e.g. one third of the total mass of hemin to be added to the fermentor was added at induction, another third is added after ¼ of the total time after fermentation has elapsed, and the last third was added half-way through the induction period). Total hemin added ranged from 50 to 300 mg/L. The fermenter was allowed to continue for 8–12 hours post-induction. At the end of this period, several 1 ml aliquots were removed from the broth for determination of hemoglobin production.

Example 2

Culture Harvest Breakage and Lysate Preparation

Cell Washing and Disruption

Cells were harvested by centrifugation at 10,000 x g for 10 minutes or they were collected by filtration by cross-flow filtration with 0.2 µm membranes (e.g., Millipore Prostak). The cells were washed or resuspended to 30% (w/v) in a 25 mM Na-borate/2 mM EDTA buffer (pH 9.3). Lysozyme (final conc. 0.02 g/L) and protease inhibitor (e.g., 1 mM benzamidine or 50,000 U/L aprotonin) were added to the preparation. The suspended cells were allowed to incubate for 30 minutes at 30°–31° C., and then were broken by one or more passes through a homogenizer such as a Gaulin Model 30-CD™ Homogenizer operated between 10 and 14 Kpsi or a Microfluidics Corp. Cell Disruptor Microfluidizer™ set at 13 Kpsi. The remainder of the process may be performed either under oxygen or nitrogen. The temperature of the lysate may be adjusted to 40°–90° C. or the solution may be utilized directly.

Filtration

The lysed cells were then titrated to above pH~6.8, preferably about 8.3, with 5N NaOH. Conductivity was adjusted to 30 Kmhos by addition of NaCl. The broken cell extract was clarified and the cell debris washed with borate buffer containing protease inhibitor (as above) by ultrafiltration. Since the hemoglobin product is soluble, it passes through the filtration membranes. Prostak permeate was filtered using Cuno Zeta Plus 90 LA (CUNO, Inc., Meriden, Conn.) to remove residual bioburden. A flocculant aid, such as polyethyleneimine or Magnafloc 573™ (polycationic flocculant) 5 ml of 50% MF 573 solution/l of lysate was then added to the lysate and the lysate was clarified by centrifugation followed by depth filtration.

Chromatography

After clarification all subsequent steps are performed in the cold (<10° C.). The solution may be purified by passage through either a strong cation exchange column (C), followed by a second strong cation exchange column (C) followed by a strong anion exchange column (A), or by passage through C, then A then C, or alternatively. A, then C then A or finally simply by passage through only one strong cation exchange column followed by A. Below we describe one possible purification scheme. The CCA column purification order is described here.

The solution from Prostak and Depth Filtration was oxygenated, then enough 10 mM sodium phosphate buffer was added to the preparation to bring the conductivity down to ≧1800 mmhos. The resulting solution was then titrated to pH 6.7–7.0 with 0.5–5N $H_3PO_4$, loaded onto a strong cation exchange column (such as BioRad Macro-Prep 50 S Column, IPF Biotechnics S-CPI or S-Spherodex columns, PerSeptive Biosystems Poros™ S or HS/MII columns, a Pharmacia S-Sepharose Fast Flow column, a TosoHaas Toyopearl™ SP-550C column, or Whatman SE52 or SE53 columns) pre-equilibrated with 10 mM sodium phosphate, washed, and then eluted with 14–20 mM sodium phosphate buffer at pH 7.4–7.7. A fraction collector can be used to collect fractions of interest. Alternatively, the solution may be further processed as described below.

A second cation exchange step can be performed. The solution from the first cation exchange step is diluted with an equal volume of deionized water, and the pH is adjusted to 6.8 with 5N phosphoric acid to provide adequate binding conditions for the second cation exchange column. A strong cation exchanger such as those listed above is used. The column is pre-equilibrated with 10 mM sodium phosphate, pH 6.8. After loading, the bound protein on the column is washed with approximately 2 column volumes of the equilibration buffer. A 14 mM sodium phosphate, pH 7.4 wash, is then used to selectively elute the protein. During elution, the column effluent is monitored for total protein by UV absorbance at 280 nm.

Anion Exchange Chromatography

The pooled peak from the second column peak fractions were concentrated and buffer exchanged into 20 mM Tris, pH 8.6 buffer using 30K NMWCO, tangential flow Filtron Centrasette diafiltration membranes (Omega type; Filtron Technology Corp., Northborough, Mass.).

The concentrated hemoglobin material was then additionally purified by means of an anion exchange column such as BioRad Macro-Prep 50 Q column, PerSeptive BioSystems Poros™ Q column, Pharmacia Q-Sepharose Fast Flow column, TosoHaas Toyopearl™ QAE-550C column, or Whatman BioSystems QA52 or DE53 column. Prior to use, the preferred column (30×20 cm=20 L Pharmacia Fast Flow Q Sepharose) was equilibrated with 20 mM Tris-HCl buffer, pH 8.6. After loading, the column was washed with at least 2 column volumes of 20 mM Tris, pH 8.3 buffer, and the protein eluted with 30 mM Tris-HCl buffer, pH 7.6. Product was collected into a depyrogenated glass vessel and samples periodically collected until an integrated methemoglobin peak was observed in the visible spectrum of the samples. The primary function of this Q-column was to complete removal of *E. coli* proteins and endotoxins.

Concentration and Buffer Exchange

After the anion exchange chromatography above (Q-chromatography), the Q-peak was concentrated subjected to the method of Example 4 for removal of $Ni^{2+}$ and other metal divalent cations.

Example 3

Removal of Nickel From Purified Hemoglobin Using Chelating Resin

Attempts were made to remove Ni from hemoglobin solutions using Sepharose Fast Flow chelating resin in the uncharged form as an adsorbent for $Ni^{2+}$. The chelating resin was equilibrated in formulation buffer (5 mM NaPi/150 mM NaCl, pH 7.4) and then the $Ni^{2+}$ containing rHB1.1 fluids were passed through the column several times. Analysis of the effluent by atomic absorption indicated that the $Ni^{2+}$ in the product stream was not significantly reduced.

Example 4

Removal of Nickel From Purified Hemoglobin Using EDTA Diafiltration

Following elution from the sepharose Q column (Example 2), the rHb1.1 was concentrated over an ultrafiltration membrane to about 4 liters volume. Then, it was diafiltered with 40 liters (ten turnover volumes) of formulation buffer (5 mM NaPi/150 mM NaCl, pH 7.4) supplemented with EDTA to 10 mM. Next, the rHb1.1 was diafiltered with formulation buffer without EDTA to remove the EDTA. Finally, the rHb1.1 was further concentrated to more than 50 mg rHb1.1/ml. Measurement of $[Ni^{2+}]$ was obtained by atomic absorption of both the permeate (buffer washed through the ultrafiltration membrane) and the retentate (the Hb-containing solution that does not permeate the membrane). This is method (1).

The EDTA/formulation buffer was made by first preparing a 1M EDTA concentrate in water for injection (WFI) using disodium EDTA. The concentrate was chilled to 0°–37° C., preferably 2°–10° C. and brought to pH 8–8.5 using stock 10N NaOH or 5N aqueous HCl, as needed. It was then sterile filtered into a depyrogenated glass vessel. The filtered EDTA concentrate was blended with formulation buffer at a volume ratio of 1:100, and the resulting EDTA/formulation buffer was maintained at 2°–10° C.

Figure 2:
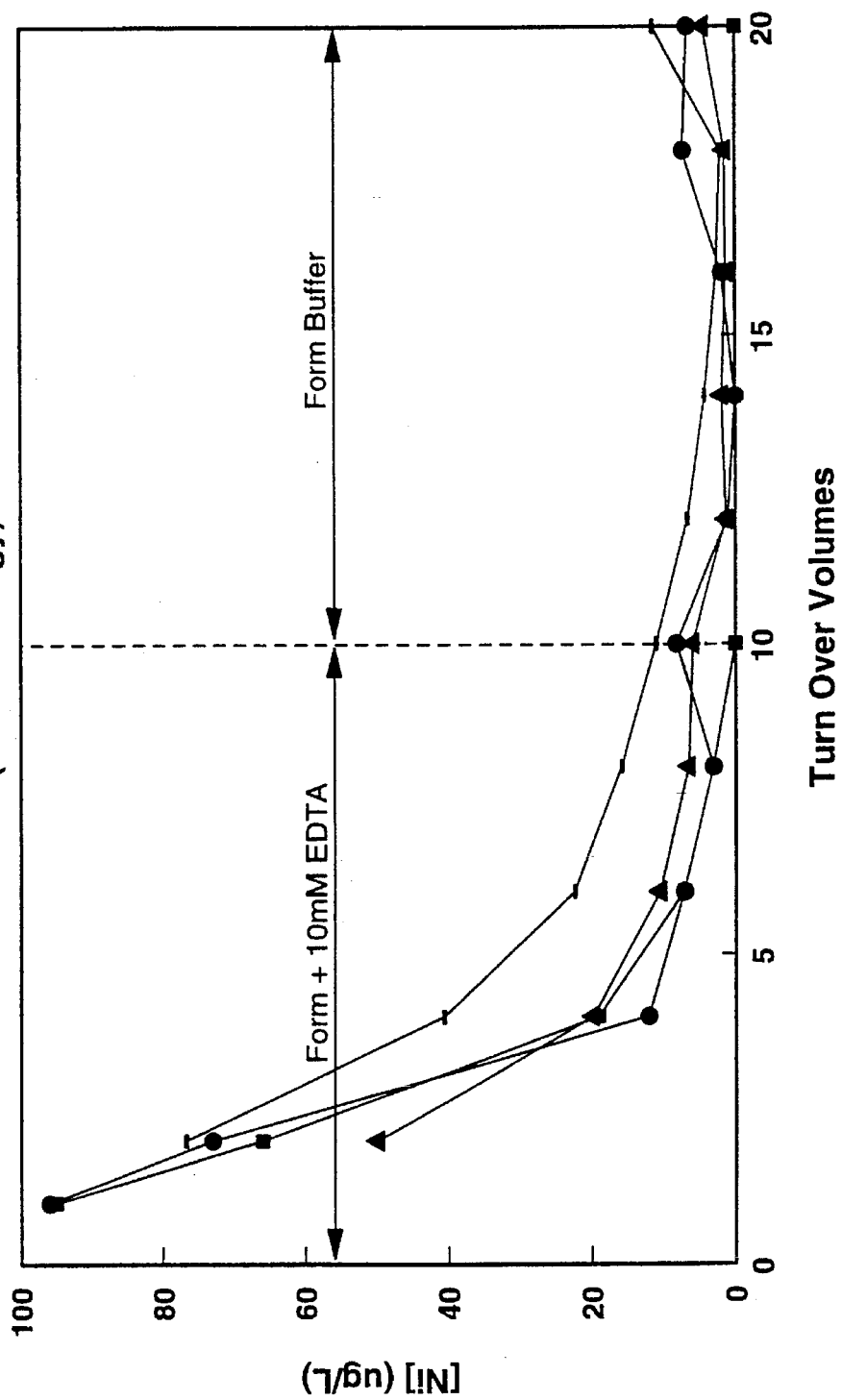
FIG. 2 shows a comparison of [$Ni^{2+}$] for Runs 1 (■), 2 (●), 4 (▲), and 5 (▬). The profiles are the [$Ni^{2+}$] in the retentate stream. Hemoglobin concentrations ([Hb]) were 22 g/L (Run 1), 32 g/L (Run 2), 22 g/l (Run 4), and 13 g/L (Run 5). The different [Hb] did not affect the effectiveness of the EDTA to washout $Ni^{2+}$ from the retentate stream.
Figure 3:
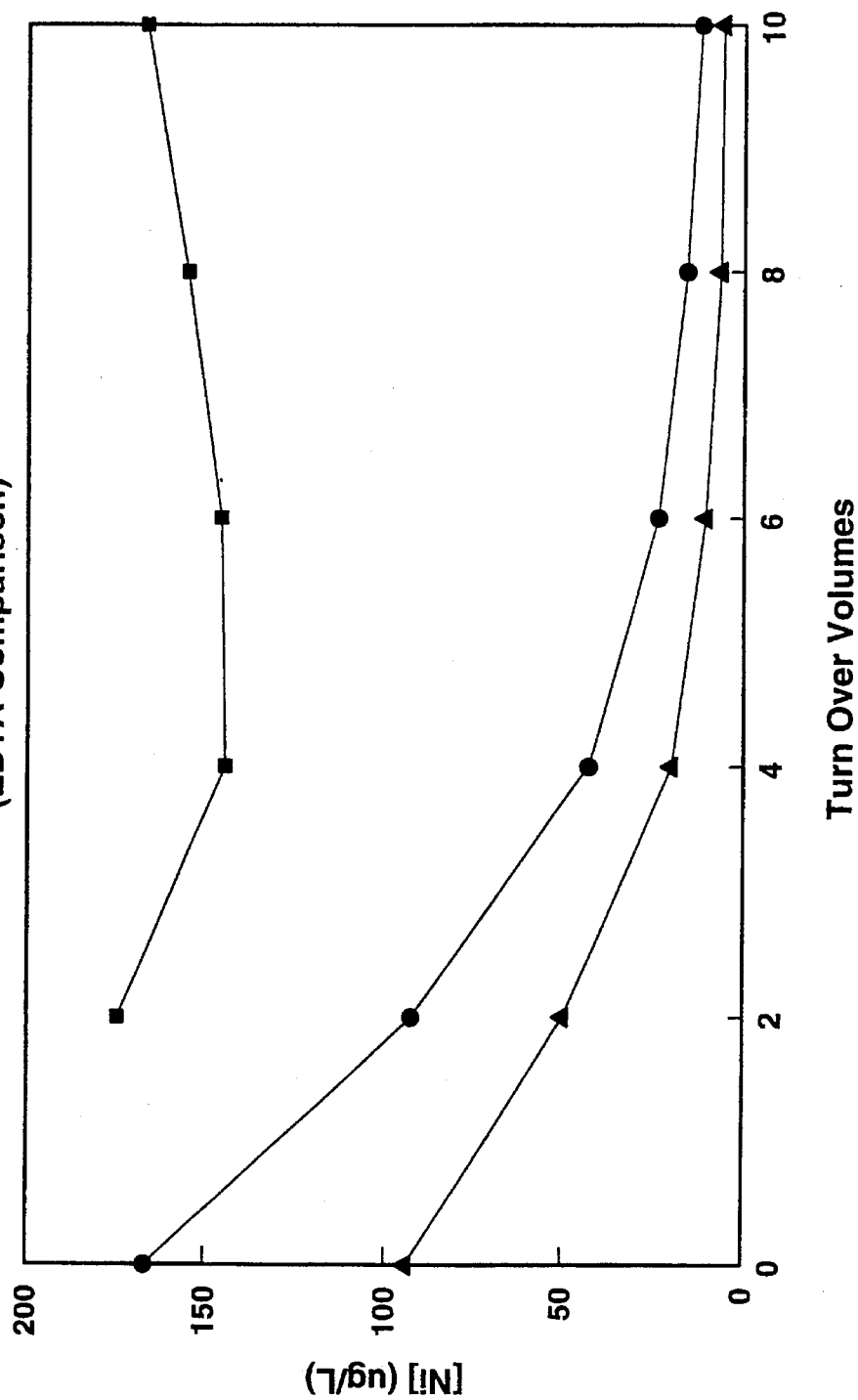
FIG. 3 shows the effect of the exchange buffer EDTA concentration on the effectiveness of removing $Ni^{2+}$ from the hemoglobin solution during diafiltration. Runs 3 (●) and 4 (▲) were run with [EDTA] of 5 mM and 10 mM respectively, while Run 3a (■) was run with no EDTA present.

The following measurements were performed on each batch of bulk:

1. color/appearance
2. P50
3. Hill coefficient
4. tryptic mapping
5. total hemoglobin
6. pH
7. high performance size exclusion chromatography (HPSEC)
8. percent methemoglobin
9. metals concentration by atomic absorption
10. chelating agent concentration Table 1 shows the results of nickel measurements of hemoglobin solutions that were purified according to the methods of Examples 1 and 2. Table 2 shows the results of nickel measurements of hemoglobin solutions that were purified according to the methods of Examples 1, 2 and 4. FIG. 1 shows the $[Ni^{2+}]$ as a function of TOV for both permeate and retentate during an EDTA ultrafiltration run (Run 1). FIG. 2 shows the $[Ni^{2+}]$ as a function of TOV for the retentate during four EDTA ultrafiltration runs (Runs 1, 2, 4, 5). FIG. 3 compares the $[Ni^{2+}]$ in the retentate for three runs wherein two of the runs (Runs 3, 4) are from FIG. 2 and the other run (Run 3a) is without EDTA in the diafiltration buffer.

TABLE 1

Nickel Concentration Without EDTA Treatment

| Batch | Nickel Concentration (µg/L) |
| --- | --- |
| A | 750 |
| B | 454 |
| C | 450 |
| D | 467 |
| E | 466 |
| F | 380 |

TABLE 2

Nickel Concentration With EDTA Treatment

| Batch | Nickel Concentration (µg/L) |
| --- | --- |
| A' | 3 |
| B' | 6.7 |
| C' | 14.3 |
| D' | 11.9 |
| E' | 14 |
| F' | 10.8 |

Although the initial method (method 1) outlined previously in this example is successful in reducing the $[Ni^{2+}]$ to acceptable levels (i.e., $[Ni^{2+}]<20$ µg/L and $Ni^{2+}/Hb<0.4$ µg/gm) it also increases the exchange buffer required. Several strategies were evaluated in an attempt to reduce the buffer demands and ease the operation of the final ultrafiltration step. These strategies are as described in the following methods (1), (2), (3), (4), and (5):

(1) The method described previously in this example using 10 TOV of EDTA buffer followed by formulation buffer (Run 5).

(2) The material from Example 2 was concentrated to the diafiltration operating volume and then EDTA was added to obtain a 10 mM EDTA concentration (10 mM EDTA spike). The solution was then diafiltered against 10 TOV of formulation buffer. $[Ni^{2+}]$ was not determined at 0 TOV; that is a sample was not taken after the EDTA addition and before diafiltration. The final $[Ni^{2+}]$ was about 13 µg/L with a $Ni^{2+}/Hb$ of about 1.3 µg/gm. (Run 7).

(3) The same procedure as (2) was used except that the target spike concentration of EDTA in the retentate was 50 mM. The $[Ni^{2+}]$ profile in the retentate was similar to that of (2) except for the significant increase of the $[Ni^{2+}]$ upon addition of the EDTA. (Run 8).

(4) Addition of EDTA to a target concentration of 10 mM was made to the dilute solution from Example 2. The solution was then concentrated to the diafiltration operating volume and then diafiltered against 10 TOV of formulation buffer. The ultrafiltration system was prerinsed with formulation buffer plus 10 mM EDTA solution prior to exposing the Hb to the system. This was done to rid the ultrafiltration system of any readily accessible $Ni^{2+}$. The final $[Ni^{2+}]$ was about 21 µg/L with a $Ni^{2+}$/Hb of about 0.8 µg/gm. (Run 10).

(5) 0.5M EDTA was added into the effluent from the Q column of Example 2 to a target [EDTA] of 10 mM, resulting in [EDTA] of approximately 5–10 mM. The effluent was then concentrated and diafiltered with 2 TOV of 10 mM EDTA, pH 7.83 in a diafiltration device that had been prerinsed with 10 mM EDTA. The solution was then diafiltered with 8 TOV of formulation buffer. The final $[Ni^{2+}]$ was about 17 µg/L. (Run 11).

Figure 4:
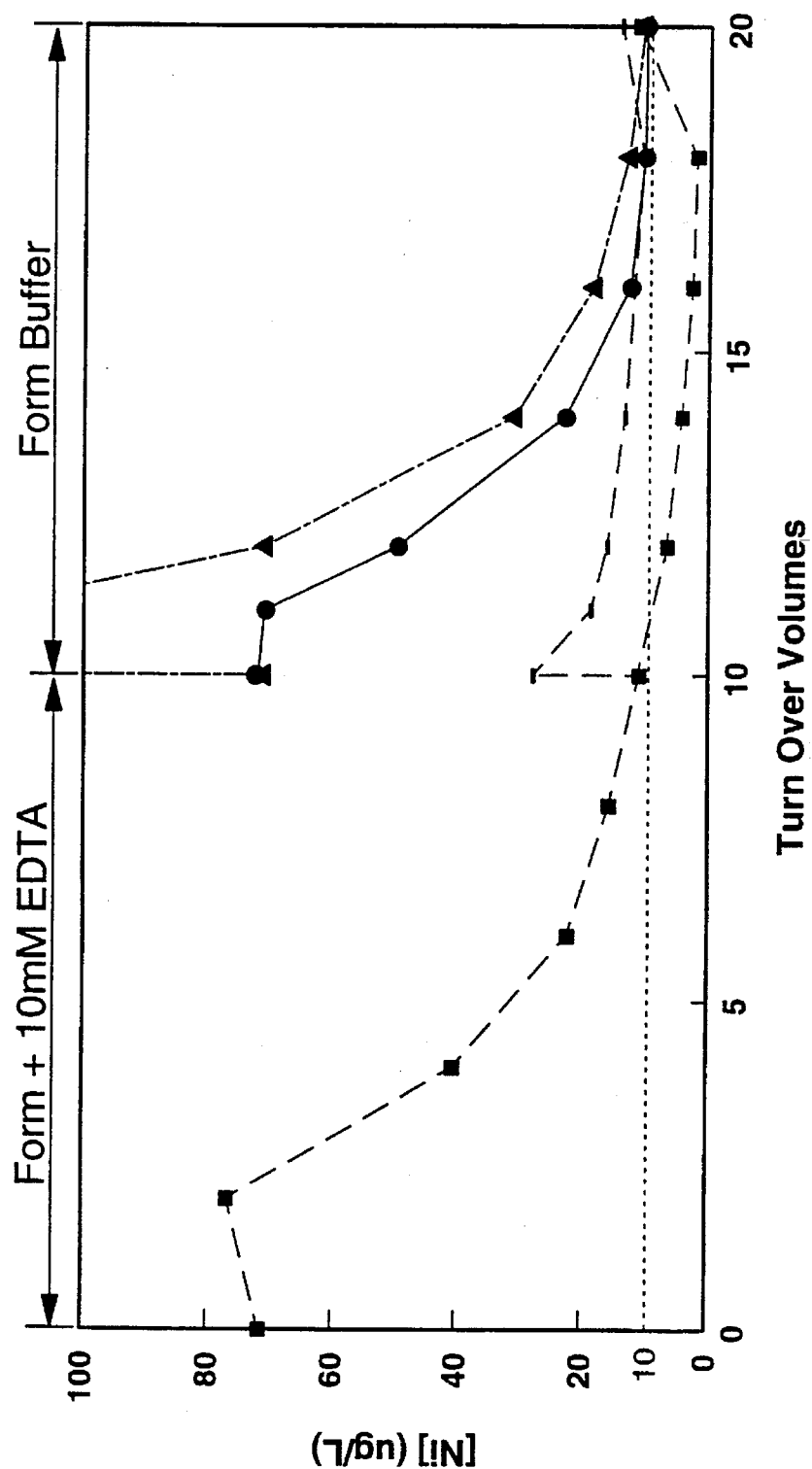
FIG. 4 shows four different strategies for using EDTA to remove $Ni^{2+}$. The four strategies are: (■) the method described in Example 4 as method (1) using 10 TOV of EDTA buffer followed by formulation buffer (Run 5); (●) in Run 7, the material from Example 2 was concentrated to the diafiltration operating volume and then EDTA was added to obtain a 10 mM EDTA concentration (10 mM EDTA spike). The solution was then diafiltered against 10 TOV of formulation buffer. [$Ni^{2+}$] was not determined at 0 turnover volume (TOV). The final [$Ni^{2+}$] was about 22 µg/L with a $Ni^{2+}$/Hb of about 1.3 µg/gm; (▲) in Run 8, the same procedure as (2) was used except that the target [EDTA] spike added at 10 TOV was 50 mM. The [$Ni^{2+}$] profile was similar to that of (2) except for the significant increase of the [$Ni^{2+}$] upon addition of the EDTA; and (▬) in Run 10, addition of EDTA to a target [EDTA] of 10 mM was made to the dilute solution from Example 2. The solution was then concentrated to the diafiltration operating volume and then diafiltered against 10 TOV of formulation buffer. The ultrafiltration system was prerinsed with a formulation plus 10 mM EDTA solution prior to exposing the Hb to the system. This was done to rid the ultrafiltration system of any readily accessible $Ni^{2+}$. The final [$Ni^{2+}$] was about 21 µ/L with a $Ni^{2+}$/Hb of about 0.8 µg/gm.

FIG. 4 shows the results for these variations. Table 3 summarizes the $Ni^{2+}$ reduction for the various Runs. The results illustrate that none of the EDTA spike runs demonstrated the ability to remove $Ni^{2+}$ from the retentate as thoroughly as the method (1) above as evidenced by the final $Ni^{2+}$ concentrations and the $Ni^{2+}$/Hb ratios. This difference in performance is because method (1) not only exposes the Hb to 10 TOV of EDTA exchange buffer but also utilizes the existing 10 mM EDTA after the initial 10 TOV to aid in the removal of the $Ni^{2+}$. Although method (1) produces lower $[Ni^{2+}]$ in final product, visual comparison of the first 10 TOV of method (1) above to the 10 TOV of methods (2) and (3) above shows that the $[Ni^{2+}]$ in methods (2) and (3) above approaches its minimum quicker than the method (1). This faster response is the result of the immediate presence of the 10 mM EDTA in the retentate stream to aid in the removal of the $Ni^{2+}$. Conversely, the lag time observed in method (1) above is the result of the time required for the EDTA concentrations to reach levels necessary to remove $Ni^{2+}$ at an appreciable rate.

TABLE 3

Nickel Removal After EDTA Treatment

| Run | [Hb] (µg/L) | % $Ni^{2+}$ Removal | Final $Ni^{2+}$/Hb | Method |
|---|---|---|---|---|
| 1 | 22 | 98 | 0.5 | method (1) |
| 2 | 32 | 95 | 0.4 | method (1) |
| 3 | 35 | 94 | 0.6 | * |
| 4 | 13 | 95 | 0.4 | method (1) |
| 5 | 13 | 97 | 0.2 | method (1) |
| 6 | 13 | −109*** | 9.1 | ** |
| 7 | 13 | 86 | 1.3 | method (2) |
| 8 | 15 | 85 | 1.0 | method (3) |
| 10 | 18 | 94 | 0.8 | method (4) |
| 11 | 13**** | ND | ND | method (5) |

Figure 5:
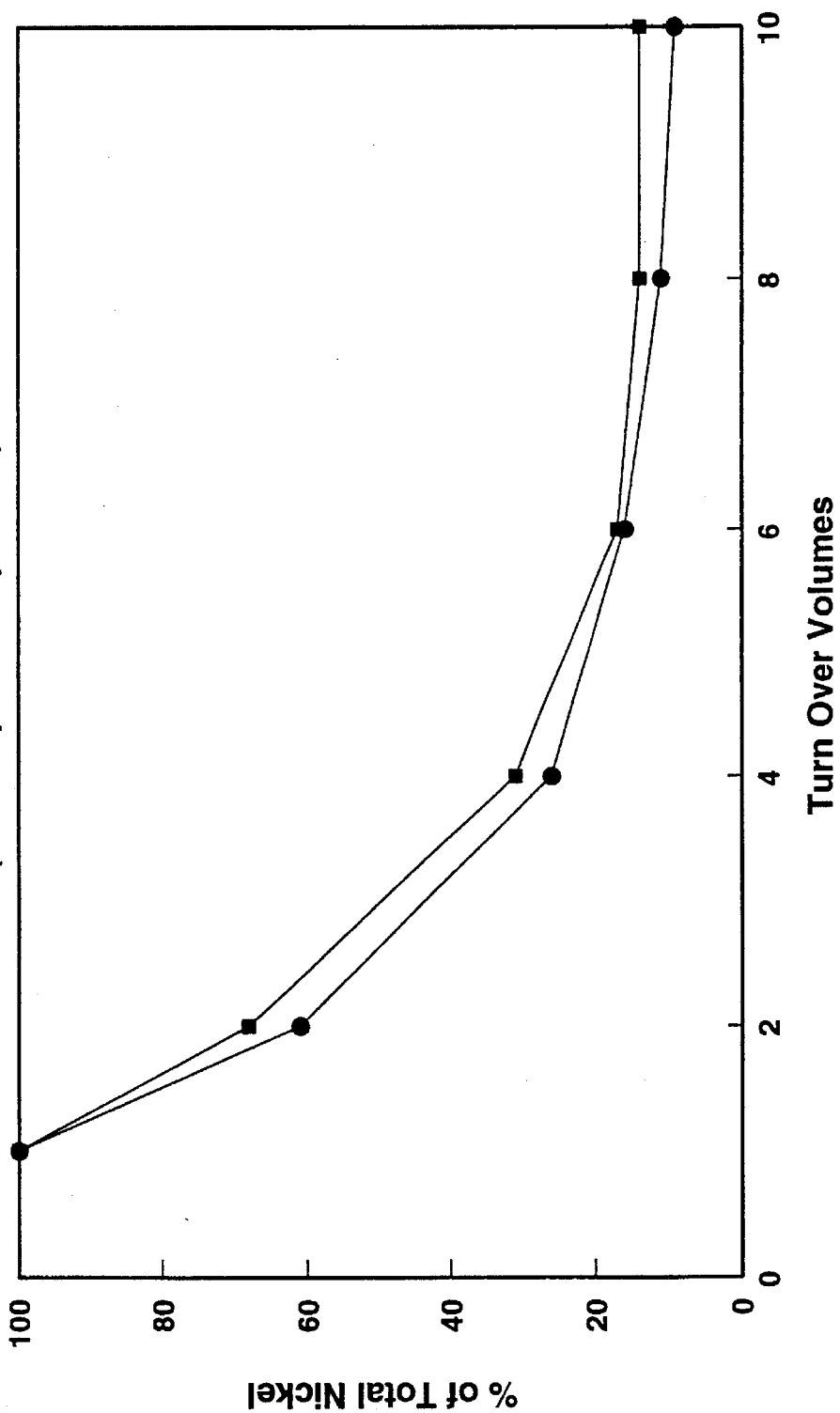
FIG. 5 shows a plot of Runs 7 (■) (10 mM EDTA spike) and 8 (●)(50 mM EDTA spike) as a percentage of the total $Ni^{2+}$ against the number of TOV and demonstrates that the [EDTA] does not influence the rate of $Ni^{2+}$ removal, so long as the [EDTA] is above a critical threshold concentration.

*10 TOV formulation buffer then 10 TOV formulation buffer plus 5 mM EDTA
**20 TOV formulation buffer alone (no EDTA)
***No removal of Ni2+; measured Ni2+ at end was 9% greater than starting concentration
****average of 3 successful runs
ND not determined FIG. 5 shows the results of Runs 7 and 8 (methods (2) and (3) above, respectively) as a percentage of total $Ni^{2+}$ against the number of TOV. The [EDTA] used in these runs did not influence the rate at which $Ni^{2+}$ is removed.

In Run 8 (method 3 above) a sample was taken after the 50 mM EDTA spike addition but prior to diafiltration. This sample revealed a 150 percent increase in the $[Ni^{2+}]$ just after the addition of EDTA to the retentate stream. This information suggested that the ultrafiltration system or its components contributed $Ni^{2+}$ to the Hb product stream. To further analyze this phenomenon, an experiment was designed to evaluate the pre-rinsing of the ultrafiltration system with a formulation plus EDTA buffer.

Figure 6:
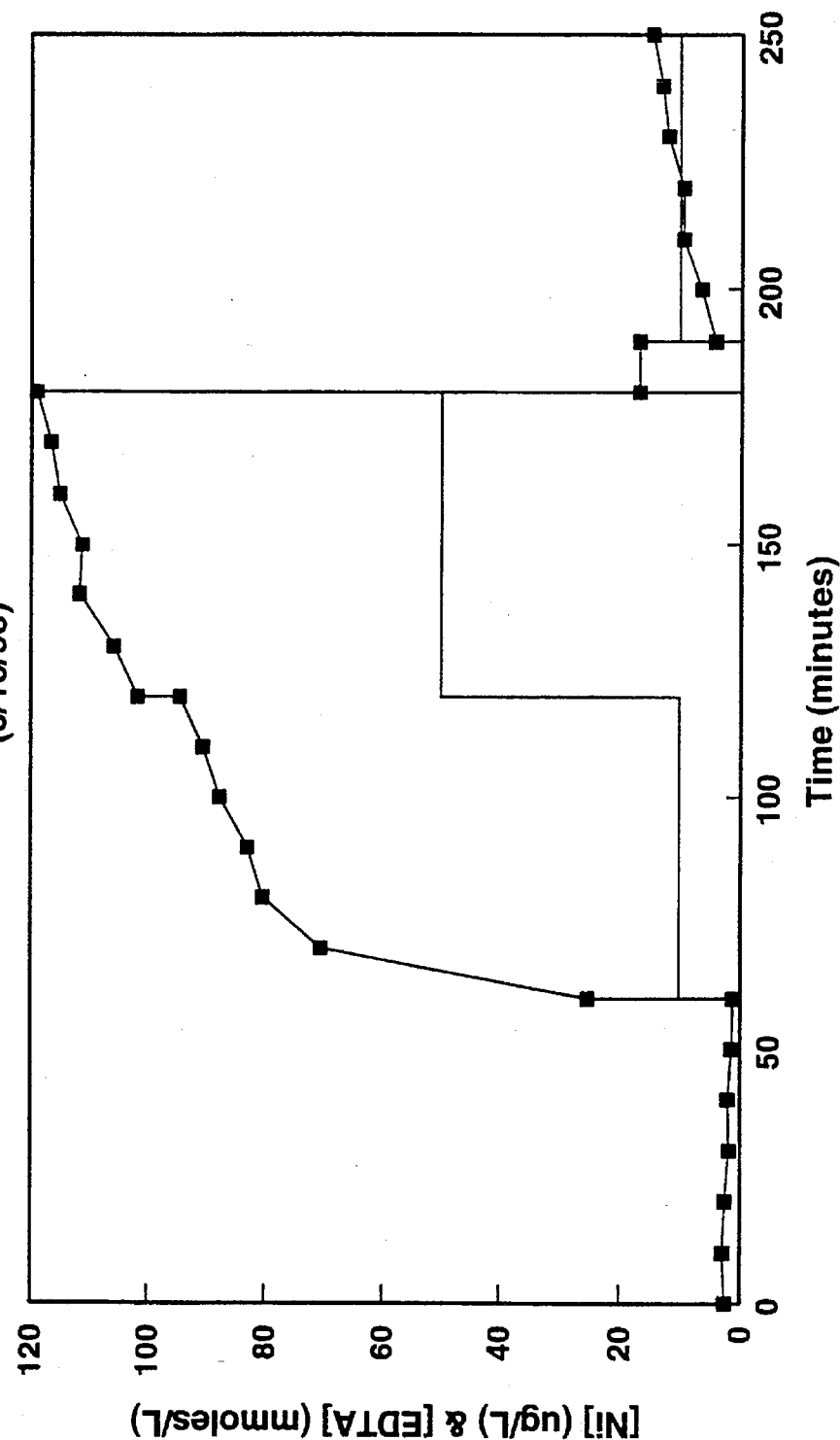
FIG. 6 shows a plot of [$Ni^{2+}$] (■) and [EDTA] ( . . . ) when ultrafiltration occurred with formulation buffer for 1 hour, followed by formulation plus 10 mM EDTA solution rinse for 1 hour, followed by addition of EDTA to obtain [EDTA] of 50 mM, followed by draining of the system and addition of formulation buffer for 10 minutes, followed by formulation buffer plus 10 mM EDTA for 1 hour.

The experiment entailed recirculation of formulation buffer for 1 hour, followed by a formulation plus 10 mM EDTA solution rinse for 1 hour. Additional EDTA was added to obtain a target EDTA concentration of 50 mM and continued recirculation for 1 additional hour. The system was then drained, rinsed with formulation buffer and then rinsed with formulation buffer plus 10 mM EDTA for 1 hour. Results of this experiment are shown in FIG. 6. FIG. 6 illustrates the following:

(a) $[Ni^{2+}]$ does not increase when formulation buffer is circulated through the ultra filtration system.

(b) $[Ni^{2+}]$ increases significantly upon addition of EDTA to the circulating formulation buffer.

(c) $[Ni^{2+}]$ rises at a steady rate 20 minutes after the introduction of the EDTA to the ultrafiltration system.

(d) EDTA concentration (10 mM versus 50 mM) does not appear to affect the rate of $Ni^{2+}$ released into the system.

(e) The initial jump in $[Ni^{2+}]$ was eliminated with the pretreatment of the ultrafiltration system with the formulation plus EDTA solution. The rate of $Ni^{2+}$ released into the system was slowed.

The results shown in FIG. 6 show that $[Ni^{2+}]$ can be washed out of the ultrafiltration system with a formulation plus EDTA solution. Additionally, the retentate streams were analyzed for [EDTA] using HPLC. The EDTA concentration data exhibited a near theoretical washout profile for both the retentate and permeate streams.

Reviewing the results from all the experiments above, the provides the following summary of conclusions:

(a) $Ni^{2+}$ can be removed from a solution containing a protein like hemoglobin by washing the protein with a formulation plus 10 mM EDTA solution.

(b) Formulation buffer alone will not significantly reduce $Ni^{2+}$ in a solution containing hemoglobin.

(c) Washing the hemoglobin may be accomplished by diafiltration in an ultrafiltration system using a 30K molecular weight cutoff membrane.

(d) A greater than 90 percent reduction in the total $Ni^{2+}$ in the hemoglobin solution may be achieved using the strategy of method (1) above.

(e) EDTA concentrations greater than or equal to 5 mM are effective in removing $Ni^{2+}$ from a hemoglobin solution.

(f) In the EDTA spike addition strategies (methods (2) and (3) above), 10 mM and 50 mM EDTA concentrations exhibited nearly equal rates of $Ni^{2+}$ removal.

(g) Hemoglobin concentration does not affect the effectiveness of EDTA to remove $Ni^{2+}$ so long as the EDTA concentration is present in sufficient amount.

(h) No significant alteration in the quality of the hemoglobin occurs during diafiltration to remove $Ni^{2+}$.

(i) The ultrafiltration system contributes $Ni^{2+}$ to the hemoglobin solution.

(j) loosely bound $Ni^{2+}$ may be washed out of the ultrafiltration system with a formulation plus 10 mM solution.

(k) EDTA exhibits zero retention in the ultrafiltration system utilized.

Example 5

Pharmaceutical Formulation of Ni free Hemoglobin

The purified essentially nickel-free hemoglobin was incorporated into a physiologically acceptable blood substitute solution. A preferred solution included the following components:

| Hgb (gm/l) | 30–120 |
|---|---|
| Sodium (mEq/l) | 135–145 |
| Potassium (mEq/l) | 3.5–4.5 |
| Chloride (mEq/l) | 90–110 |

Preferably, the solution has a pH of 7.3–7.5, an osmolality of 280–310, and an oncotic pressure of 20–30 mm Hg. Osmolality is controlled by concentration of hemoglobin and of the electrolytes, as well as by the optional ingredient glucose (preferably 0–30 gm/l). The oncotic pressure is controlled by the concentration of the hemoglobin and by its degree of crosslinking. Agents, such as albumin (0–70 gm/l), dextran (0–100 gm/l) and polyethylene glycol (0–25 gm/l) may be added to increase oncotic pressure. Moreover, to reduce the degree of methemoglobin formation, anti-oxidant or free radical scavengers, such as mannitol (0–20 gm/l), glutathione (0–4 gm/l), ascorbic acid (0–1.3 gm/l) and vitamin E (0–100 IU/l) may be provided.

If a low oxygen affinity mutant hemoglobin is employed, it may be desirable or necessary to adjust the $P_{50}$ of the solution to the preferred level by suitable choice of electrolytes, pH and other characteristics of the composition. Preferably, the final solution has a $P_{50}$ of 24–40 torr under standard physiological conditions.

A particularly preferred pharmaceutical composition of essentially nickel-free hemoglobin for use as a blood substitute is:

| Hgb (gm/l) | 50 |
|---|---|
| NaPO$_4$ (mM) | 5 |
| NaCl (mM) | 150 |
| pH | 7.3 |

Alternatively, the essentially nickel-free hemoglobin is formulated as a drug delivery vehicle.

Example 6

Administration of Ni free Hemoglobin to Rabbits

Nickel has been hypothesized to increase vasoconstriction of coronary vessels during myocardial infarction (Rubanyi et al., (1981) J. Mol. Cellular Cardiology 13:1023–1026; Rubanyi et al., (1981) Ann. Clin. Lab. Sci. 11(1):93) and to stimulate the contraction of smooth muscle (Rubanyi and Balogh, (1982) Am J. Obstet. Gynecol. 142:1016–1020). Consequently, the effect of essentially nickel free hemoglobin on contraction of various smooth muscle was analyzed.

After an overnight fast, New Zealand white rabbits were anesthetized using i.p. urethane at a dose of 2 g/kg. A tracheotomy was performed for ventilation, and a catheter containing heparinized saline (10 U/ml) was placed into the right carotid artery for continuous monitoring of blood pressure. A second catheter was placed into the internal jugular vein for i.v. hemoglobin administration. A custom-made dent sleeve catheter with a diameter of 2.5 mm and a sleeve length of 24 mm was placed through the mouth and the sleeve positioned in the lower esophageal sphincter (LES) by the pull-through technique to determine the high pressure zone. The catheter was continuously perfused at a rate of 1.032 ml/hour and pressure monitored continuously, using a side channel from the infusion catheter connected to a pressure transducer (Spectramed model P23XL; Viggo-Spectramed Inc., Critical Care Div., Oxnard, Calif.) and a polygraph (model 2400, Gould Electronics, Cleveland, Ohio).

Dose responsive effects of hemoglobin purified according to Example 2 were determined. Dosage ranged from about 10 to about 50 ml of 50 mg/ml concentration. The dose responsive effects of this hemoglobin is compared to the effect of $N^G$-nitro-L-arginine methyl ester (L-NAME), an antagonist of NO-synthase. The dose of L-NAME (10 mg/kg) is known to be effective in inhibiting relaxation of the guinea pig gallbladder. Some experiments are performed in animals pre-treated with sodium nitroprusside (a non-enzymatic NO donor) to determine if this can reverse the LES effects of the nickel-containing hemoglobin and L-NAME. The concentration used (2 mg/kg) reverses the effects of L-NAME in other systems. In additional experiments, excess NO synthase substrate (1-arginine, 300 mg/kg and 3000 mg/g) was administered in an attempt to reverse the effects of nickel-containing hemoglobin. The lower dose reverses the effects of L-NAME in other systems. The inactive enantiomer, D-arginine is used at equal doses as a negative control. To establish that the effects of nickel-containing hemoglobin on the LES is not secondary to blood pressure effects, the effect of the vasopressor agent phenylephrine on LES pressure at doses (100–1000 ng/kg/min) that mimic the pressor effect of nickel-containing hemoglobin was investigated. Any pressor effects were minor. All drugs were administered in 0.9 percent NaCl. Six animals were usually used for each protocol to allow statistical analysis of variance.

The dose responsive LES effects of nickel-containing hemoglobin purified according to Example 2 were then compared to LES effects of nickel-containing hemoglobin purified according to Examples 2 and 4 (essentially nickel-free hemoglobin). The results show that purifying hemoglobin according to Examples 2 and 4 decreases LES effects.

Example 7

Administration of Ni free Hemoglobin to Opossum and Opossum Muscle

Nickel has been hypothesized to increase vasoconstriction of coronary vessels during myocardial infarction (Rubanyi et at., (1981) J. Mol. Cellular Cardiology 13:1023–1026; Rubanyi et at., (1981) Ann. Clin. Lab. Sci. 11(1):93) and to stimulate the contraction of smooth muscle (Rubanyi and Balogh, (1982) Am J. Obstet. Gynecol. 142:1016–1020). Consequently, the effect of essentially nickel free hemoglobin on contraction of various smooth muscle was analyzed.

Measurement of the effect of nickel-containing hemoglobin is measured in opossums either in vitro by administration of the hemoglobin to isolated esophageal muscle or in vivo by administration of the hemoglobin to the animal.

Measuring Mechanical Activity of Esophageal Muscle

Strips of esophageal muscle devoid of submucosa and measuring 3 cm in length by 3 mm in width are cut from the circumferential axis of the esophagus of the opossum. They are placed in electrode clips with one end of the strip held in a Plexiglas clip and the other end attached by a silk suture to a Radnoti force displacement transducer. The transducers are mounted on rack-and-pinion assemblies that allow the strips to be stretched in increments. When in place, the strips lay between 2 platinum wire stimulating electrodes spaced 4 mm apart, The stimulating electrodes are attached to the output Grass S8800 stimulators. The muscle strips and electrode clips are lowered into jacketed tissue baths that contain Krebs solution that is warmed to 37° C. and aerated with 5% $CO_2$—95% $O_2$. Outputs of the force-displacement transducers are connected to A to D converters in a MacLab recording system. The data are stored and analyzed in a Macintosh IIci computer. Muscle strips are stretched slowly in a stepwise fashion to the length for optimal response ($L_0$), and allowed to equilibrate for 60 min. Intrinsic esophageal nerves are stimulated by 2–3 sec trains of electrical pulses (0.5 milliseconds duration, 50 Volt amplitude, at 2–3 Hz). These stimuli produce a 50–70 percent maximal response, allowing changes induced by experimental manipulations to be easily identified. In these studies, each muscle strip serves as its own control. Results are expressed as a percent change from control. Statistical comparisons are made with the Student's t-test or multivariate analysis as is appropriate.

The effect of hemoglobin on muscle contraction is determined by adding increasing concentrations of hemoglobin purified according to the methods of Example 2 to the tissue bath. This effect is then compared to the muscle contraction observed from administration of hemoglobin purified according to the methods of Examples 2 and 4.

Measuring Swallow-induced Peristalsis

Adult opossums of either sex are fasted overnight. They are anesthetized with intramuscular injections of a 20:1 mixture of ketamine-acepromazine (50 mg/kg). The animals are strapped supine on an animal board, and a six lumen manometry assembly is introduced into the esophagus through a bite block. The lower esophageal sphincter (LES) is located by pulling the catheter across the gastroesophageal junction. Swallows are induced by stroking the throat or cricoid cartilage. Manometric recordings are made from 30 min. before through 3–5 hours after the intravenous infusion of hemoglobin. Dosage is from about 10 to about 50 ml of 50 mg/ml concentration. Control infusions of human serum albumin are used. The amplitude, duration and rate of propagation of swallow-induced peristaltic contractions are observed. Any spontaneous activity is also noted. The resting tone of the LES is monitored, and the amplitude and duration of swallow-induced LES relaxation is evaluated over time.

The effect of hemoglobin on muscle contraction is determined by administration of concentrations of hemoglobin purified according to the methods of Examples 2 to the opossum. This effect is then compared to the muscle contraction observed from administration of hemoglobin purified according to the methods of Examples 2 and 4.

Example 8

Administration of Nickel-free Hemoglobin to Humans

Twenty-two (22) human volunteers received rHb1.1 purified according to Example 2 and formulated according to Example 5. These volunteers were dosed with rHb1.1 at four dose levels, ranging from 0.05 g/kg to 0.18 g/kg (16 of the 22 received 0.15 g/kg) by intravenous infusion at a rate up to 3.75 ml/kg/hr. Therefore, the largest dose of rHb1.1 was administered in 48 minutes. A control group of 4 volunteers received human serum albumin as a control. Three of the volunteers that received the rHb1.1 had symptoms of mild urticaria (14 percent).

A different set of human volunteers received 0.15 g/kg of essentially nickel-free rHb1.1 purified according to Examples 2 and 4 and formulated according to Example 5. Administration was by intravenous infusion up to a maximum of 48 minutes. The number of human subjects was 15. Subjects were monitored post-infusion. These volunteers receiving essentially nickel-free hemoglobin showed no evidence of urticaria.

What is claimed is:

1. A method for obtaining essentially nickel-free hemoglobin comprising removal of nickel from a nickel-containing hemoglobin solution by exposing the nickel-containing hemoglobin solution to a chelating agent for sufficient time to allow chelating of significant nickel, followed by removal of the chelating agent.

2. A method for obtaining essentially nickel-free hemoglobin according to claim 1 wherein said chelating agent is a multidentate acetic acid based chelator.

3. A method for obtaining essentially nickel-free hemoglobin according to claim 2 wherein said multidentate acetic acid based chelator is selected from the group consisting of EDTA, DPTA, TTHA and EGTA.

4. A method for obtaining essentially nickel-free hemoglobin according to claim 3 wherein said multidentate acetic acid based chelator is EDTA.

5. A method for obtaining essentially nickel-free hemoglobin according to claim 1 wherein said exposing the nickel-containing hemoglobin solution to a chelating agent is by diafiltration with a chelating agent solution.

6. A method for obtaining essentially nickel-free hemoglobin according to claim 5 wherein said chelating agent solution is at least 1 mM in chelating agent.

7. A method for obtaining essentially nickel-free hemoglobin according to claim 6 wherein said chelating agent solution is from about 5 to about 10 mM in chelating agent.

8. A method for obtaining essentially nickel-free hemoglobin according to claim 5 wherein said chelating agent solution is an amount of at least 5 turnover volumes.

9. A method for obtaining essentially nickel-free hemoglobin according to claim 6 wherein said chelating agent solution is an amount of at least 5 turnover volumes.

10. A method for obtaining essentially nickel-free hemoglobin according to claim 7 wherein said chelating agent solution is an amount of at least 5 turnover volumes.

11. A method for obtaining essentially nickel-free hemoglobin according to claim 5 wherein said chelating agent solution is an amount of at least 10 turnover volumes.

12. A method for obtaining essentially nickel-free hemoglobin according to claim 6 wherein said chelating agent solution is an amount of at least 10 turnover volumes.

13. A method for obtaining essentially nickel-free hemoglobin according to claim 7 wherein said chelating agent solution is an amount of at least 10 turnover volumes.

14. A method for obtaining essentially nickel-free hemoglobin according to claim 1 wherein said sufficient time to allow chelating of significant nickel is time sufficient to remove at least 80 percent of the nickel from the nickel-containing hemoglobin solution.

15. A method for obtaining essentially nickel-free hemoglobin according to claim 14 wherein said sufficient time to allow chelating of significant nickel is time sufficient to remove at least 90 percent of the nickel from the nickel-containing hemoglobin solution.

16. A method for obtaining essentially nickel-free hemoglobin according to claim 15 wherein said sufficient time to allow chelating of significant nickel is time sufficient to remove at least 95 percent of the nickel from the nickel-containing hemoglobin solution.

17. A method for obtaining essentially nickel-free hemoglobin according to claim 5 wherein said sufficient time to allow chelating of significant nickel is time sufficient to remove at least 80 percent of the nickel from the nickel-containing hemoglobin solution.

18. A method for obtaining essentially nickel-free hemoglobin according to claim 17 wherein said sufficient time to allow chelating of significant nickel is time sufficient to remove at least 90 percent of the nickel from the nickel-containing hemoglobin solution.

19. A method for obtaining essentially nickel-free hemoglobin according to claim 18 wherein said sufficient time to allow chelating of significant nickel is time sufficient to remove at least 95 percent of the nickel from the nickel-containing hemoglobin solution.

20. A method for obtaining essentially nickel-free hemoglobin according to claim 1 wherein said removal of the chelating agent is by diafiltration with formulation buffer.

21. A method for obtaining essentially nickel-free hemoglobin according to claim 20 wherein said formulation buffer is a chelating agent solution minus chelating agent.

22. A method for obtaining essentially nickel-free hemoglobin according to claim 4 wherein said removal of the chelating agent is by diafiltration with formulation buffer.

23. A method for obtaining essentially nickel-free hemoglobin according to claim 22 wherein said formulation buffer is a chelating agent solution minus chelating agent.

24. A method for obtaining essentially nickel-free hemoglobin according to claim 5 wherein said removal of the chelating agent is by diafiltration with formulation buffer.

25. A method for obtaining essentially nickel-free hemoglobin according to claim 1 wherein said nickel-containing hemoglobin solution is obtained by a process selected from the group consisting of large scale fermentation and purification.

26. A method for obtaining essentially nickel-free hemoglobin according to claim 1 wherein said nickel-containing hemoglobin solution is obtained by a large scale fermentation and/or purification process.

27. A method for obtaining essentially nickel-free hemoglobin according to claim 1 wherein said nickel-containing hemoglobin solution comprises hemoglobin selected from the group consisting of recombinant hemoglobin and mutant hemoglobin.

28. A method for obtaining essentially nickel-free hemoglobin according to claim 27 wherein said nickel-containing hemoglobin solution comprises hemoglobin selected from the group consisting of recombinant hemoglobin and mutant hemoglobin.

29. A method for obtaining essentially nickel-free hemoglobin comprising removal of nickel from a nickel-containing hemoglobin solution by diafiltering the nickel-containing hemoglobin solution with at least 5 turnover volumes of at least 5 mM EDTA in a formulation buffer for sufficient time to allow chelating of at least 80 percent of nickel in the nickel-containing hemoglobin solution, followed by removal of the chelating agent by diafiltering with formulation buffer.

30. A method for obtaining essentially nickel-free hemoglobin comprising removal of nickel from a nickel-containing hemoglobin solution by diafiltering the nickel-containing hemoglobin solution with at least 10 turnover volumes of at least 10 mM EDTA in a formulation buffer for sufficient time to allow chelating of at least 90 percent of nickel in the nickel-containing hemoglobin solution, followed by removal of the chelating agent by diafiltering with formulation buffer.

* * * * *

UNITED STATES PATENT AND TRADEMARK OFFICE
CERTIFICATE OF CORRECTION

PATENT NO. : 5,578,564
DATED : November 26, 1996
INVENTOR(S) : Mark L. Chivers & Thomas K. Belval It is certified that error appears in the above-indentified patent and that said Letters Patent is hereby corrected as shown below:

Please cancel claim 26.

In claim 28, line 2, delete "27" and substitute -- 25 --.

Please add the following claims:

31. A method for obtaining essentially nickel-free hemoglobin according to claim 24 wherein said formulation buffer is a chelating agent solution minus chelating agent.

32. A method for obtaining essentially nickel-free hemoglobin according to claim 30 wherein diafiltering occurs for sufficient time to allow chelating of at least 95 percent of nickel in the nickel-containing hemoglobin.

Signed and Sealed this

Eighteenth Day of March, 1997

Attest:

BRUCE LEHMAN

*Attesting Officer*  *Commissioner of Patents and Trademarks*